United States Patent
Lynch et al.

(10) Patent No.: US 9,827,143 B2
(45) Date of Patent: *Nov. 28, 2017

(54) SHUNT DEVICE AND METHOD FOR TREATING OCULAR DISORDERS

(71) Applicant: GLAUKOS CORPORATION, San Clemente, CA (US)

(72) Inventors: Mary G. Lynch, Atlanta, GA (US); Reay H. Brown, Atlanta, GA (US)

(73) Assignee: Glaukos Corporation, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,885

(22) Filed: Nov. 11, 2016

(65) Prior Publication Data

US 2017/0216095 A1    Aug. 3, 2017

Related U.S. Application Data

(60) Continuation of application No. 14/316,605, filed on Jun. 26, 2014, now Pat. No. 9,492,320, which is a
(Continued)

(51) Int. Cl.
*A61F 9/007* (2006.01)
*A61M 25/00* (2006.01)
*A61F 9/00* (2006.01)

(52) U.S. Cl.
CPC ....... *A61F 9/00781* (2013.01); *A61M 25/007* (2013.01); *A61M 25/0068* (2013.01);
(Continued)

(58) Field of Classification Search
CPC ................ A61F 9/00781; A61F 2/04; A61M 2250/0067; A61M 25/007
(Continued)

(56) References Cited

U.S. PATENT DOCUMENTS

| 2,031,754 A | 2/1936 | Mills |
| 2,127,903 A | 8/1938 | Bowen |

(Continued)

FOREIGN PATENT DOCUMENTS

| AU | 200072059 A1 | 7/2001 |
| AU | 2004264913 | 12/2011 |

(Continued)

OTHER PUBLICATIONS

Fine, Ben S., et al., "A Clinicopathologic Study of Four Cases of Primary Open-Angle Glaucoma Compared to Normal Eyes", American Journal of Ophthalmology, vol. 91, No. 1, 1981, pp. 88-105.
(Continued)

*Primary Examiner* — Leslie Deak
(74) *Attorney, Agent, or Firm* — Knobbe Martens Olson & Bear, LLP

(57) ABSTRACT

Shunt devices and a method for continuously decompressing elevated intraocular pressure in eyes affected by glaucoma by diverting excess aqueous humor from the anterior chamber of the eye into Schlemm's canal where post-operative patency can be maintained with an indwelling shunt device which surgically connects the canal with the anterior chamber. The shunt devices provide uni- or bi-directional flow of aqueous humor into Schlemm's canal.

42 Claims, 6 Drawing Sheets

Related U.S. Application Data continuation of application No. 12/966,889, filed on Dec. 13, 2010, now Pat. No. 8,771,217, which is a division of application No. 10/987,114, filed on Nov. 12, 2004, now Pat. No. 7,850,637, which is a continuation of application No. 10/445,740, filed on May 27, 2003, now Pat. No. 6,827,700, which is a continuation of application No. 10/242,385, filed on Sep. 12, 2002, now Pat. No. 6,626,858, which is a continuation of application No. 09/558,505, filed on Apr. 26, 2000, now Pat. No. 6,450,984.

(60) Provisional application No. 60/131,030, filed on Apr. 26, 1999.

(52) U.S. Cl.
CPC ..... *A61F 9/0017* (2013.01); *A61F 2230/0008* (2013.01); *A61F 2250/0067* (2013.01); *A61M 25/0074* (2013.01); *A61M 2210/0612* (2013.01)

(58) Field of Classification Search
USPC .................................................. 604/8
See application file for complete search history.

(56) References Cited

U.S. PATENT DOCUMENTS

| | | |
|---|---|---|
| 3,159,161 A | 12/1964 | Ness |
| 3,717,151 A | 2/1973 | Collett |
| 3,788,327 A | 1/1974 | Donowitz et al. |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Aklyama |
| 3,948,871 A | 4/1976 | Butterfield et al. |
| 4,037,604 A | 7/1977 | Newkirk |
| 4,043,346 A | 8/1977 | Mobley et al. |
| 4,113,088 A | 9/1978 | Binkhorst |
| 4,168,697 A | 9/1979 | Cantekin |
| 4,175,563 A | 11/1979 | Arenberg et al. |
| 4,325,375 A | 4/1982 | Nevyas |
| 4,402,681 A | 9/1983 | Haas et al. |
| 4,428,746 A | 1/1984 | Mendez |
| 4,449,974 A | 5/1984 | Messingschlager |
| 4,457,757 A | 7/1984 | Molteno |
| 4,501,274 A | 2/1985 | Skjaerpe |
| 4,521,210 A | 6/1985 | Wong |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,846,172 A | 7/1989 | Berlin |
| 4,846,793 A | 7/1989 | Leonard et al. |
| 4,853,224 A | 8/1989 | Wong |
| 4,863,457 A | 9/1989 | Lee |
| 4,883,864 A | 11/1989 | Scholz |
| 4,886,488 A | 12/1989 | White |
| 4,900,300 A | 2/1990 | Lee |
| 4,936,825 A | 6/1990 | Ungerleider |
| 4,946,436 A | 8/1990 | Smith |
| 4,955,900 A | 9/1990 | Higashi et al. |
| 4,968,296 A | 11/1990 | Ritch et al. |
| 4,986,810 A | 1/1991 | Semrad |
| 4,997,652 A | 3/1991 | Wong |
| 5,005,577 A | 4/1991 | Frenekl |
| 5,041,081 A | 8/1991 | Odrich |
| 5,057,098 A | 10/1991 | Zelman |
| 5,073,163 A | 12/1991 | Lippman |
| 5,092,837 A | 3/1992 | Ritch et al. |
| 5,095,887 A | 3/1992 | Leon et al. |
| 5,116,327 A | 5/1992 | Seder et al. |
| 5,127,901 A | 7/1992 | Odrich |
| 5,129,895 A | 7/1992 | Vassiliadis et al. |
| 5,139,502 A | 8/1992 | Berg et al. |
| 5,164,188 A | 11/1992 | Wong |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,246,451 A | 9/1993 | Trescony et al. |
| 5,248,231 A | 9/1993 | Denham et al. |
| 5,290,295 A | 3/1994 | Querals et al. |
| 5,300,020 A | 4/1994 | L'Esperance, Jr. |
| 5,318,513 A | 6/1994 | Leib et al. |
| 5,326,345 A | 7/1994 | Price, Jr. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,796 A | 10/1995 | Krupin |
| 5,472,440 A | 12/1995 | Beckman |
| 5,476,445 A | 12/1995 | Baerveldt et al. |
| 5,486,165 A | 1/1996 | Stegmann |
| 5,516,522 A | 5/1996 | Peyman et al. |
| 5,520,631 A | 5/1996 | Nordquist et al. |
| 5,557,453 A | 9/1996 | Schalz et al. |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,601,094 A | 2/1997 | Reiss |
| 5,601,549 A | 2/1997 | Miyagi |
| 5,626,558 A | 5/1997 | Suson |
| 5,626,559 A | 5/1997 | Solomon |
| 5,639,278 A | 6/1997 | Dereume et al. |
| 5,651,782 A | 7/1997 | Simon et al. |
| 5,651,783 A | 7/1997 | Reynard |
| 5,665,114 A | 9/1997 | Weadock et al. |
| 5,670,161 A | 9/1997 | Healy et al. |
| 5,676,679 A | 10/1997 | Simon et al. |
| 5,681,275 A | 10/1997 | Ahmed |
| 5,681,323 A | 10/1997 | Arick |
| 5,702,414 A | 12/1997 | Richter et al. |
| 5,702,419 A | 12/1997 | Berry et al. |
| 5,704,907 A | 1/1998 | Nordquist et al. |
| 5,709,854 A | 1/1998 | Griffith-Cima et al. |
| 5,713,844 A | 2/1998 | Peyman |
| 5,722,948 A | 3/1998 | Gross |
| 5,723,005 A | 3/1998 | Herrick |
| 5,725,529 A | 3/1998 | Nicholson et al. |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,785,674 A | 7/1998 | Mateen |
| 5,800,376 A | 9/1998 | Vaskelis |
| 5,807,302 A | 9/1998 | Wandel |
| 5,810,870 A | 9/1998 | Myers et al. |
| 5,824,071 A | 10/1998 | Nelson et al. |
| 5,824,072 A | 10/1998 | Wong |
| 5,830,139 A | 11/1998 | Abrue |
| 5,830,171 A | 11/1998 | Wallace |

(56) References Cited

U.S. PATENT DOCUMENTS

| | | |
|---|---|---|
| 5,833,694 A | 11/1998 | Poncet |
| 5,836,939 A | 11/1998 | Negus et al. |
| 5,840,041 A | 11/1998 | Petter et al. |
| 5,865,831 A | 2/1999 | Cozean et al. |
| 5,868,697 A | 2/1999 | Richter et al. |
| 5,879,319 A | 3/1999 | Pynson et al. |
| 5,882,327 A | 3/1999 | Jacob |
| 5,886,822 A | 3/1999 | Spitzer |
| 5,893,837 A | 4/1999 | Eagles et al. |
| 5,908,449 A | 6/1999 | Bruchman et al. |
| 5,913,852 A | 6/1999 | Magram |
| 5,932,299 A | 8/1999 | Katoot |
| 5,980,928 A | 11/1999 | Terry |
| 5,981,598 A | 11/1999 | Tatton |
| 6,004,302 A | 12/1999 | Brierley |
| 6,007,510 A | 12/1999 | Nigam |
| 6,007,511 A | 12/1999 | Prywes |
| 6,033,434 A | 3/2000 | Borghi |
| 6,045,557 A | 4/2000 | White et al. |
| 6,050,970 A | 4/2000 | Baeverldt |
| 6,050,999 A | 4/2000 | Paraschac et al. |
| 6,059,772 A | 5/2000 | Hsia et al. |
| 6,059,812 A | 5/2000 | Clerc et al. |
| 6,063,116 A | 5/2000 | Kelleher |
| 6,063,396 A | 5/2000 | Kelleher |
| 6,071,286 A | 6/2000 | Mawad |
| 6,077,299 A | 6/2000 | Adelberg et al. |
| 6,102,045 A | 8/2000 | Nordquist et al. |
| 6,123,668 A | 9/2000 | Abreu |
| 6,142,990 A | 11/2000 | Burk |
| 6,146,387 A | 11/2000 | Trott et al. |
| 6,165,210 A | 12/2000 | Lau et al. |
| 6,168,575 B1 | 1/2001 | Soltanpour |
| 6,174,305 B1 | 1/2001 | Mikus et al. |
| 6,186,974 B1 | 2/2001 | Allan et al. |
| 6,187,016 B1 | 2/2001 | Hedges et al. |
| 6,193,656 B1 | 2/2001 | Jeffries et al. |
| 6,197,056 B1 | 3/2001 | Schachar |
| 6,228,873 B1 | 5/2001 | Brandt et al. |
| 6,231,597 B1 | 5/2001 | Deem et al. |
| 6,241,721 B1 | 6/2001 | Cozean et al. |
| 6,251,090 B1 | 6/2001 | Avery et al. |
| 6,254,612 B1 | 7/2001 | Hieshima |
| 6,261,256 B1 | 7/2001 | Ahmed |
| 6,266,182 B1 | 7/2001 | Morita |
| 6,268,398 B1 | 7/2001 | Ghosh et al. |
| 6,287,256 B1 | 9/2001 | Park et al. |
| 6,287,313 B1 | 9/2001 | Sasso |
| 6,299,895 B1 | 10/2001 | Hammang et al. |
| 6,306,114 B1 | 10/2001 | Freeman et al. |
| 6,331,313 B1 | 12/2001 | Wong et al. |
| 6,342,058 B1 | 1/2002 | Portney |
| 6,348,042 B1 | 2/2002 | Warren, Jr. |
| 6,355,033 B1 | 3/2002 | Moorman et al. |
| 6,358,222 B1 | 3/2002 | Grundei |
| 6,361,519 B1 | 3/2002 | Knudson et al. |
| 6,375,642 B1 | 4/2002 | Grieshaber et al. |
| 6,416,777 B1 | 7/2002 | Yaacobi |
| 6,428,501 B1 | 8/2002 | Reynard |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,494,857 B1 | 12/2002 | Neuhann |
| 6,508,779 B1 | 1/2003 | Suson |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,579,235 B1 | 6/2003 | Abita et al. |
| 6,579,256 B2 | 6/2003 | Hughes |
| 6,582,453 B1 | 6/2003 | Tran et al. |
| 6,585,680 B2 | 7/2003 | Bugge |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,622,473 B2 | 9/2003 | Lynch et al. |
| 6,623,283 B2 | 9/2003 | Torigian et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,213 B2 | 12/2003 | Svadovskiy |
| 6,666,841 B2 | 12/2003 | Gharib et al. |
| 6,682,500 B2 | 1/2004 | Soltanpour et al. |
| 6,699,211 B2 | 3/2004 | Savage |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,893,413 B2 | 5/2005 | Martin |
| 6,955,656 B2 | 10/2005 | Bergheim et al. |
| 6,962,573 B1 | 11/2005 | Wilcox |
| 6,966,888 B2 | 11/2005 | Cullen et al. |
| 6,981,958 B1 | 1/2006 | Gharib et al. |
| 7,033,603 B2 | 4/2006 | Nelson et al. |
| 7,041,077 B2 | 5/2006 | Shields |
| 7,077,848 B1 | 7/2006 | de Juan et al. |
| 7,094,225 B2 | 8/2006 | Tu et al. |
| 7,101,402 B2 | 9/2006 | Phelps et al. |
| 7,135,009 B2 | 11/2006 | Tu et al. |
| 7,144,616 B1 | 12/2006 | Unger et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,192,484 B2 | 3/2007 | Chappa et al. |
| 7,220,238 B2 | 5/2007 | Lynch et al. |
| 7,273,475 B2 | 9/2007 | Tu et al. |
| 7,294,115 B1 | 11/2007 | Wilk |
| 7,297,130 B2 | 11/2007 | Bergheim et al. |
| 7,331,984 B2 | 2/2008 | Tu et al. |
| 7,364,564 B2 | 4/2008 | Sniegowski |
| 7,431,710 B2 | 10/2008 | Tu et al. |
| 7,488,303 B1 | 2/2009 | Haffner et al. |
| RE40,722 E | 6/2009 | Chappa |
| 7,563,241 B2 | 7/2009 | Tu et al. |
| 7,641,627 B2 | 1/2010 | Camras et al. |
| 7,678,065 B2 | 3/2010 | Haffner et al. |
| 7,695,135 B1 | 4/2010 | Rosenthal |
| 7,708,711 B2 | 5/2010 | Tu et al. |
| 7,811,268 B2 | 10/2010 | Maldon Ado Bas |
| 7,815,592 B2 | 10/2010 | Coroneo |
| 7,850,637 B2 | 12/2010 | Lynch et al. |
| 7,850,638 B2 | 12/2010 | Coroneo |
| 7,857,782 B2 | 12/2010 | Tu et al. |
| 7,862,531 B2 | 1/2011 | Yaron et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,951,155 B2 | 5/2011 | Smedley et al. |
| 7,997,460 B2 | 8/2011 | Badawi et al. |
| 8,007,459 B2 | 8/2011 | Haffner et al. |
| 8,034,016 B2 | 10/2011 | Yaron et al. |
| 8,034,105 B2 | 10/2011 | Stegmann et al. |
| 8,062,244 B2 | 11/2011 | Tu et al. |
| 8,075,511 B2 | 12/2011 | Tu et al. |
| 8,118,768 B2 | 2/2012 | Tu et al. |
| 8,128,588 B2 | 3/2012 | Coroneo |
| 8,142,364 B2 | 3/2012 | Haffner et al. |
| 8,152,752 B2 | 4/2012 | Lynch et al. |
| 8,267,882 B2 | 9/2012 | Euteneuer et al. |
| 8,267,995 B2 | 9/2012 | Castillejos |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,388,568 B2 | 3/2013 | Lynch et al. |
| 8,439,972 B2 | 5/2013 | Badawi et al. |

(56) References Cited

U.S. PATENT DOCUMENTS

| | | |
|---|---|---|
| 8,579,846 B2 | 12/2013 | Tu et al. |
| 8,617,094 B2 | 12/2013 | Smedley et al. |
| 8,656,958 B2 | 2/2014 | Unger et al. |
| 8,771,217 B2 | 7/2014 | Lynch et al. |
| 8,801,648 B2 | 8/2014 | Bergheim et al. |
| 8,808,219 B2 | 8/2014 | Bergheim et al. |
| 8,814,820 B2 | 8/2014 | Bergheim et al. |
| 8,882,781 B2 | 11/2014 | Smedley et al. |
| 9,066,782 B2 | 6/2015 | Tu et al. |
| 9,155,654 B2 | 10/2015 | Tu et al. |
| 9,173,775 B2 | 11/2015 | Haffner et al. |
| 9,220,632 B2 | 12/2015 | Smedley et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,597,230 B2 | 3/2017 | Haffner et al. |
| 2001/0000527 A1 | 4/2001 | Yaron et al. |
| 2001/0025150 A1 | 9/2001 | De Juan, Jr. et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0072673 A1 | 6/2002 | Yamamoto et al. |
| 2002/0082591 A1 | 6/2002 | Haefliger |
| 2002/0087111 A1 | 7/2002 | Ethier et al. |
| 2002/0099434 A1 | 7/2002 | Buscemi et al. |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0169468 A1 | 11/2002 | Brown |
| 2002/0177856 A1 | 11/2002 | Richter et al. |
| 2002/0193725 A1 | 12/2002 | Odrich |
| 2003/0019833 A1 | 1/2003 | Unger et al. |
| 2003/0055372 A1 | 3/2003 | Lynch et al. |
| 2003/0060752 A1 | 3/2003 | Bergheim et al. |
| 2003/0079329 A1 | 5/2003 | Yaron et al. |
| 2003/0093084 A1 | 5/2003 | Nissan et al. |
| 2003/0097151 A1 | 5/2003 | Smedley et al. |
| 2003/0135149 A1 | 7/2003 | Cullen et al. |
| 2003/0139729 A1 | 7/2003 | Stegmann et al. |
| 2003/0153863 A1 | 8/2003 | Patel |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0212383 A1 | 11/2003 | Cote et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0000499 A1 | 1/2004 | Maiola et al. |
| 2004/0015140 A1 | 1/2004 | Shields |
| 2004/0024345 A1 | 2/2004 | Gharib et al. |
| 2004/0059248 A1 | 3/2004 | Messner et al. |
| 2004/0076676 A1 | 4/2004 | Tojo et al. |
| 2004/0088048 A1 | 5/2004 | Richter et al. |
| 2004/0092856 A1 | 5/2004 | Dahan |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0162545 A1 | 8/2004 | Brown et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0215126 A1 | 10/2004 | Ahmed |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2005/0038498 A1 | 2/2005 | Dubrow et al. |
| 2005/0049578 A1 | 3/2005 | Tu et al. |
| 2005/0055075 A1 | 3/2005 | Pinchuk et al. |
| 2005/0107734 A1 | 5/2005 | Coroneo |
| 2005/0119601 A9 | 6/2005 | Lynch et al. |
| 2005/0119737 A1 | 6/2005 | Bene et al. |
| 2005/0125003 A1 | 6/2005 | Pinchuk et al. |
| 2005/0171507 A1 | 8/2005 | Christian et al. |
| 2005/0182350 A1 | 8/2005 | Nigam |
| 2005/0184004 A1 | 8/2005 | Rodgers et al. |
| 2005/0192527 A1 | 9/2005 | Gharib et al. |
| 2005/0240143 A1 | 10/2005 | Dohlman |
| 2005/0250788 A1 | 11/2005 | Tu et al. |
| 2005/0261624 A1 | 11/2005 | Wilcox |
| 2005/0267397 A1 | 12/2005 | Bhalla |
| 2005/0267398 A1 | 12/2005 | Protopsaltis et al. |
| 2005/0273033 A1 | 12/2005 | Grahn et al. |
| 2005/0277864 A1 | 12/2005 | Haffner et al. |
| 2005/0288619 A1 | 12/2005 | Savage |
| 2006/0032507 A1 | 2/2006 | Tu |
| 2006/0036207 A1 | 2/2006 | Koonmen et al. |
| 2006/0079828 A1 | 4/2006 | Brown |
| 2006/0116626 A1 | 6/2006 | Smedley et al. |
| 2006/0129129 A1 | 6/2006 | Smith |
| 2006/0155300 A1 | 7/2006 | Stamper et al. |
| 2006/0173397 A1 | 8/2006 | Tu et al. |
| 2006/0200113 A1 | 9/2006 | Haffner et al. |
| 2006/0235367 A1 | 10/2006 | Takashima et al. |
| 2006/0276739 A1 | 12/2006 | Brown |
| 2007/0004998 A1 | 1/2007 | Rodgers et al. |
| 2007/0073390 A1 | 3/2007 | Lee |
| 2007/0078371 A1 | 4/2007 | Brown et al. |
| 2007/0093740 A1 | 4/2007 | Shetty |
| 2007/0106199 A1 | 5/2007 | Krivoy et al. |
| 2007/0106200 A1 | 5/2007 | Levy |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0154621 A1 | 7/2007 | Raad |
| 2007/0156079 A1 | 7/2007 | Brown |
| 2007/0179426 A1 | 8/2007 | Selden |
| 2007/0185468 A1 | 8/2007 | Prywes |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0219632 A1 | 9/2007 | Castillejos |
| 2007/0260201 A1 | 11/2007 | Prausnitz et al. |
| 2007/0276315 A1 | 11/2007 | Haffner |
| 2007/0282245 A1 | 12/2007 | Tu et al. |
| 2007/0292470 A1 | 12/2007 | Thornton |
| 2007/0292474 A1 | 12/2007 | Hsu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0039931 A1 | 2/2008 | Jelle et al. |
| 2008/0082078 A1 | 4/2008 | Berlin |
| 2008/0108932 A1 | 5/2008 | Rodgers |
| 2008/0108934 A1 | 5/2008 | Berlin |
| 2008/0125691 A1 | 5/2008 | Yaron et al. |
| 2008/0161741 A1 | 7/2008 | Bene et al. |
| 2008/0161907 A1 | 7/2008 | Chen et al. |
| 2008/0200860 A1 | 8/2008 | Tu et al. |
| 2008/0210322 A1 | 9/2008 | Unger et al. |
| 2008/0221501 A1 | 9/2008 | Cote et al. |
| 2008/0236669 A1 | 10/2008 | Unger et al. |
| 2008/0243243 A1 | 10/2008 | Williams et al. |
| 2008/0243247 A1 | 10/2008 | Poley et al. |
| 2008/0277007 A1 | 11/2008 | Unger et al. |
| 2008/0289710 A1 | 11/2008 | Unger et al. |
| 2009/0036818 A1 | 2/2009 | Grahn et al. |
| 2009/0043321 A1 | 2/2009 | Conston et al. |
| 2009/0076436 A2 | 3/2009 | Gharib et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0132040 A1 | 5/2009 | Frion et al. |
| 2009/0137992 A1 | 5/2009 | Mallakrishnan |
| 2009/0151422 A1 | 6/2009 | Unger et al. |
| 2009/0177138 A1 | 7/2009 | Brown et al. |
| 2009/0204053 A1 | 8/2009 | Nissan et al. |
| 2009/0227934 A1 | 9/2009 | Eutenever et al. |
| 2009/0275924 A1 | 11/2009 | Lattanzio et al. |

(56) References Cited

U.S. PATENT DOCUMENTS

| | | |
|---|---|---|
| 2009/0287136 A1 | 11/2009 | Castillejos |
| 2009/0326432 A1 | 12/2009 | Schmidt et al. |
| 2010/0004635 A1 | 1/2010 | Lin et al. |
| 2010/0025613 A1 | 2/2010 | Tai et al. |
| 2010/0042209 A1 | 2/2010 | Guarnieri |
| 2010/0056977 A1 | 3/2010 | Wandel |
| 2010/0056979 A1 | 3/2010 | Smedley et al. |
| 2010/0057055 A1 | 3/2010 | Camras et al. |
| 2010/0087774 A1 | 4/2010 | Haffner et al. |
| 2010/0106073 A1 | 4/2010 | Haffner et al. |
| 2010/0114006 A1 | 5/2010 | Baerveldt |
| 2010/0121342 A1 | 5/2010 | Schieber et al. |
| 2010/0125237 A1 | 5/2010 | Schocket |
| 2010/0168644 A1 | 7/2010 | Brown |
| 2010/0175767 A1 | 7/2010 | Unger et al. |
| 2010/0185138 A1 | 7/2010 | Yaron et al. |
| 2010/0191103 A1 | 7/2010 | Stamper et al. |
| 2010/0191329 A1 | 7/2010 | Badawi et al. |
| 2010/0222733 A1 | 9/2010 | Schieber et al. |
| 2010/0234791 A1 | 9/2010 | Lynch et al. |
| 2010/0241046 A1 | 9/2010 | Pinchuk et al. |
| 2010/0249691 A1 | 9/2010 | Van der Mooren et al. |
| 2010/0274259 A1 | 10/2010 | Yaron et al. |
| 2011/0009874 A1 | 1/2011 | Wardle et al. |
| 2011/0009958 A1 | 1/2011 | Wardle et al. |
| 2011/0046536 A1 | 2/2011 | Stegmann et al. |
| 2011/0046728 A1 | 2/2011 | Shareef et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0092878 A1 | 4/2011 | Tu et al. |
| 2011/0098627 A1 | 4/2011 | Wilcox |
| 2011/0098809 A1 | 4/2011 | Wardle et al. |
| 2011/0105987 A1 | 5/2011 | Bergheim et al. |
| 2011/0118649 A1 | 5/2011 | Stegmann et al. |
| 2011/0118835 A1 | 5/2011 | Silvestrini et al. |
| 2011/0130831 A1 | 6/2011 | Badawi et al. |
| 2011/0144559 A1 | 6/2011 | Lafdi et al. |
| 2011/0196487 A1 | 8/2011 | Badawi et al. |
| 2011/0224597 A1 | 9/2011 | Stegmann et al. |
| 2011/0244014 A1 | 10/2011 | Williams et al. |
| 2011/0245753 A1 | 10/2011 | Sunalp |
| 2011/0248671 A1 | 10/2011 | Dos Santos et al. |
| 2011/0257623 A1 | 10/2011 | Marshall et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0059461 A1 | 3/2012 | Badawi et al. |
| 2012/0078158 A1 | 3/2012 | Haffner et al. |
| 2012/0089072 A1 | 4/2012 | Cunningham, Jr. |
| 2012/0089073 A1 | 4/2012 | Cunningham, Jr. |
| 2012/0130467 A1 | 5/2012 | Selden et al. |
| 2012/0179087 A1 | 7/2012 | Schieber et al. |
| 2012/0184892 A1 | 7/2012 | Bigler et al. |
| 2012/0203160 A1 | 8/2012 | Kahook et al. |
| 2012/0289883 A1 | 11/2012 | Meng et al. |
| 2012/0302861 A1 | 11/2012 | Marshall et al. |
| 2012/0310072 A1 | 12/2012 | Grieshaber |
| 2012/0323159 A1 | 12/2012 | Wardle et al. |
| 2013/0006164 A1 | 1/2013 | Yaron et al. |
| 2013/0006165 A1 | 1/2013 | Eutenener et al. |
| 2013/0018295 A1 | 1/2013 | Haffner et al. |
| 2013/0079701 A1 | 3/2013 | Schieber et al. |
| 2013/0090534 A1 | 4/2013 | Burns et al. |
| 2013/0102949 A1 | 4/2013 | Baerveldt |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0150779 A1 | 6/2013 | Field |
| 2013/0150959 A1 | 6/2013 | Shieber et al. |
| 2013/0158381 A1 | 6/2013 | Rickard |
| 2013/0158462 A1 | 6/2013 | Wardle et al. |
| 2013/0165840 A1 | 6/2013 | Orge |
| 2013/0172804 A1 | 7/2013 | Schieber et al. |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0281910 A1 | 10/2013 | Tu et al. |
| 2014/0034607 A1 | 2/2014 | Meng et al. |
| 2014/0046437 A1 | 2/2014 | Renke |
| 2014/0052046 A1 | 2/2014 | Peartree et al. |
| 2014/0276332 A1 | 9/2014 | Crimaldi et al. |
| 2015/0223981 A1 | 8/2015 | Smedley et al. |
| 2015/0374546 A1 | 12/2015 | Hill |

FOREIGN PATENT DOCUMENTS

| | | |
|---|---|---|
| AU | 2009251058 B2 | 12/2013 |
| CA | 1273151 A1 | 8/1990 |
| CA | 2244646 A1 | 2/1999 |
| CA | 2442652 | 1/2011 |
| CA | 2683224 C | 12/2014 |
| CH | 92111244 | 7/1993 |
| DE | 19840047 A1 | 3/2000 |
| DE | 100 42 310 A1 | 3/2002 |
| EP | 0858788 A1 | 8/1998 |
| EP | 0898947 | 3/1999 |
| EP | 0898947 A2 | 3/1999 |
| EP | 1114627 A1 | 7/2001 |
| EP | 1977724 A1 | 10/2008 |
| EP | 2260803 A2 | 12/2010 |
| EP | 2260804 A2 | 12/2010 |
| EP | 2263621 A1 | 12/2010 |
| EP | 2351589 | 8/2011 |
| EP | 2982354 A1 | 2/2016 |
| EP | 2985012 A1 | 2/2016 |
| FR | 2710269 A1 | 3/1995 |
| FR | 2721499 | 12/1995 |
| FR | 2757068 A1 | 6/1998 |
| GB | 2296663 A | 7/1996 |
| JP | 11-123205 | 5/1999 |
| JP | 3703721 | 7/2005 |
| JP | 4031836 B2 | 1/2008 |
| JP | 4688444 | 2/2011 |
| JP | 2012-198134 | 9/2012 |
| JP | 5255402 | 4/2013 |
| JP | 5323011 | 7/2013 |
| JP | 2013-208434 | 10/2013 |
| JP | 2014-193366 | 10/2014 |
| JP | 2014-240022 | 12/2014 |
| RU | 2143250 | 12/1999 |
| WO | WO 89/00869 A1 | 2/1989 |
| WO | WO 91/18568 A1 | 12/1991 |
| WO | WO 92/00112 | 1/1992 |
| WO | WO 94/13234 | 6/1994 |
| WO | WO 94/13234 A1 | 6/1994 |
| WO | WO 94/21205 A1 | 9/1994 |
| WO | WO 95/08310 A1 | 3/1995 |
| WO | WO 96/20742 A1 | 7/1996 |
| WO | WO 98/23237 A1 | 6/1998 |
| WO | WO 98/30181 A1 | 7/1998 |
| WO | WO 98/35639 A1 | 8/1998 |
| WO | WO 98/37831 | 9/1998 |
| WO | WO 99/26567 A1 | 6/1999 |
| WO | WO 99/30641 A1 | 6/1999 |
| WO | WO 00/13627 A1 | 3/2000 |
| WO | WO 00/64389 A1 | 11/2000 |
| WO | WO 00/64390 A1 | 11/2000 |
| WO | WO 00/64391 A1 | 11/2000 |
| WO | WO 00/64393 A1 | 11/2000 |
| WO | WO 00/72788 A1 | 12/2000 |
| WO | WO 01/41685 | 6/2001 |
| WO | WO 01/50943 A2 | 7/2001 |
| WO | WO 01/68016 A2 | 9/2001 |
| WO | WO 01/78631 A2 | 10/2001 |
| WO | WO 01/97727 | 12/2001 |

(56) References Cited

FOREIGN PATENT DOCUMENTS

| WO | WO 02/36052 | 5/2002 |
|----|----|----|
| WO | WO 02/056758 | 7/2002 |
| WO | WO 02/074052 A2 | 9/2002 |
| WO | WO 02/080811 | 10/2002 |
| WO | WO 02/102274 A2 | 12/2002 |
| WO | WO 03/015659 A2 | 2/2003 |
| WO | WO 03/041622 | 5/2003 |
| WO | WO 03/045290 A1 | 6/2003 |
| WO | WO 03/073968 A2 | 9/2003 |
| WO | WO 08/061043 A2 | 5/2008 |
| WO | WO 10/135369 | 11/2010 |
| WO | WO 11/020633 A1 | 2/2011 |
| WO | WO 12/071476 | 5/2012 |
| WO | WO 13/148275 | 10/2013 |
| WO | WO 2017/030917 | 2/2017 |

OTHER PUBLICATIONS

Johnson, et al., *Schlemm's Canal Becomes Smaller After Successful Filtration Surgery*, (reprinted) ARCM Ophthalmol/vol. 118, Sep. 2000 (www.archophthalmol.com) p. 1251-1256.
Klemm, A. Balazs, J. Draeger, R. Wiezorrek, *Experimental use of spacer-retaining substances with extended duration: functional and morphological results*, Graefe's Arch Clin Exp Ophthalmol (1995) 233:592-597.
Mermoud, A., et al., "Comparison of deep sclerectomy with collagen implant and trabeculectomy in open-angle glaucoma", J. Cataracat Refract. Surg., vol. 25, No. 3, Mar. 1999, pp. 323-331 (abstract only).
Moses, Robert A., M.D.; Circumferential Flow in Schlemm's Canal; American Journal of Ophthalmology, Sep. 1979, vol. 88, No. 3, Part II, pp. 585-591.
Shields, M. Bruce, MD, *A Study Guide for Glaucoma: Aqueous Humor Dynamics*, Copyright 1982, pp. 6-43.
Tun, et al., Assessment of Trabecular Meshwork Width Using Swept Source Optical Coherence Tomography, 251:6 Graefes Arch. Clin. Exp. Ophthalmol. 1587 (2013).
International Search Report and Written Opinion in PCT/US2016/053570 dated Mar. 9, 2017.
Expert Report of M. Bruce Shields, M.D. (Mar. 9, 2015) (785 pages).
Supplemental Expert Report of M. Bruce Shields MD Regarding Invalidity of Various Claims of Glaukos' Patents-in-Suit (May 8, 2015) (105 pages).
De Juan et al., "Refinements in microinstrumentation for vitrous surgery," Am. J. Ophthalmol. 109:218-20 (1990).
Oatts et al., "In vitro an in vivo comparison of two suprachoroidal shunts," Invest. Opthalmol. Vis. Sci. 54:5416-23 (2013).
Spiegel, Detlev et al., "Schlemm's Canal Implant: A New Method to Lower Intraocular Pressure in Patients With POAG?" Ophthalmic Surgery and Lasers, vol. 30, No. 6, Jun. 1999.
Spiegel, Detlev, "Benefits and Risks of Ophthalmological Treatment" Bucherei des Augenarztes / The Ophthalmologist's Library, vol. 139, Oct. 15, 1998.
Wilcox, Michael J. et al., "Hypothesis for Improving Accessory Filtration by Using Geometry" Journal of Glaucoma, vol. 3, No. 3, 1994.
Wilcox, Michael J. et al., "Performance of a New, Low-volume, High-Surface Area Aqueous Shunt in Normal Rabbit Eyes" Journal of Glaucoma, vol. 9 No. 1, Feb. 2000, pp. 74-82.
Notice of Opposition filed Jul. 17, 2017 in EP Application No. EP 2260804.
Excerpt from the prosecution history of U.S. Appl. No. 09/549,350, including the Inventor Declaration (dated Aug./Sep. 2000).
Excerpt from the prosecution history of U.S. Appl. No. 09/704,276, including the Inventor Declaration (dated Feb. 2001).
Excerpt from the prosecution history of U.S. Pat. No. 7,857,782, including the Inventor Declaration dated Jun. 14, 2002.
Excerpt from the prosecution history of U.S. Pat. No. 8,075,511, including the Inventor Declaration dated Jun. 14, 2002.
Excerpt from the prosecution history of U.S. Pat. No. 8,579,846, including the Inventor Declaration dated Jun. 14, 2002.
Excerpts from the file history of U.S. Pat. No. 7,563,241 dated Mar. 13, 2009.
Complaint for Declaratory Judgment of Patent Non-Infringement and Invalidity (May 10, 2013).
Answer and Counterclaim (May 31, 2013).
Plaintiff Transcend Medical Inc.'s Answer to Counterclaims (Jun. 24, 2013).
Excerpt of Transcend's First Set of Interrogatories to Defendant Glaukos Corporation dated Jul. 16, 2013.
Excerpt of Transcend's First Set of Requests for Production to Defendant Glaukos Corporation dated Jul. 16, 2013.
Transcend Medical, Inc.'s Initial Disclosures, Served Jul. 30, 2013.
Glaukos Corporation's Initial Disclosures, Served Jul. 30, 2013.
Glaukos Corporation's Responses to Transcend Medical, Inc.'s First Set of Interrogatories (Nos. 1-11) (Aug. 15, 2013).
Transcend Medical, Inc.'s Responses and Objections to Glaukos Corporation's First Set of Interrogatories dated Oct. 24, 2013.
Transcend Medical, Inc.'s Disclosures Pursuant to Default Discovery Rule 4(d) (Dec. 6, 2013) (341 pages).
First Amended Complaint for Declaratory Judgment of Patent Non-Infringement and Invalidity, Filed Dec. 16, 2013.
Transcend Medical, Inc.'s First Supplemental Response to Glaukos Corporation's Interrogatory No. 1 dated Dec. 23, 2013.
Redacted Exhibits A-C of Transcend Medical, Inc.'s First Supplemental Response to Glaukos Corporation's Interrogatory No. 1 dated Dec. 23, 2013.
Answer and Counterclaim, Filed Jan. 3, 2014.
Transcend Medical, Inc.'s Answer to Counterclaims, Served Jan. 13, 2014.
Subpoena to Produce Documents, Information, or Objects or to Permit Inspection of Premises in a Civil Action propounded on Dr. Richard A. Hill, Feb. 11, 2014.
Transcend Medical, Inc.'s First Supplemental Invalidity Contentions (Mar. 3, 2014) (107 pages).
Transcend Medical, Inc.'s Second Supplemental Response to Glaukos Corporation's Interrogatory No. 1 dated Mar. 3, 2014.
Petition to Correct Inventorship in a Patent Pursuant to 35 U.S.C. § 256 and 37 C.F.R. § 1.324, filed in the prosecution history of U.S. Pat. No. 7,857,782 dated May 2014.
Petition to Correct Inventorship in a Patent Pursuant to 35 U.S.C. § 256 and 37 C.F.R. § 1.324, filed in the prosecution history of U.S. Pat. No. 8,075,511 dated May 2014.
Petition to Correct Inventorship in a Patent Pursuant to 35 U.S.C. § 256 and 37 C.F.R. § 1.324, filed in the prosecution history of U.S. Pat. No. 8,579,846 dated May 2014.
Communication of the Board of Appeal Pursuant to Article 15(1) of the Rules of Procedure of the Boards of Appeal, submitted in the prosecution history of EP1977724, dated May 8, 2014 (Board of Appeal Communication, EP1977724.
Transcend's First Supplemental Response to Glaukos Corporation's Interrogatory Nos. 17 and 18 dated May 13, 2014.
Transcend Medical, Inc's Responses and Objections to Glaukos Corporation's Second Set of Interrogatories dated May 27, 2014.
Request for Correction of Inventorship Under 37 C.F.R. § 1.48(d), dated May 27, 2014 and filed in the prosecution history of U.S. Appl. No. 60/281,973.
Excerpts from the certified Deposition Transcript of David Haffner, dated May 28, 2014.
Excerpts from the certified Deposition Transcript of Barbara Niksch, dated Jun. 6, 2014.
Joint Claim Construction Statement, Filed Jun. 20, 2014.
Glaukos Corporation's Responses to Transcend Medical, Inc.'s Second Set of Interrogatories (No. 12) dated Jun. 26, 2014.
Glaukos Corporation's Responses to Transcend Medical, Inc.'s Third Set of Interrogatories (No. 13) dated Jul. 7, 2014.
Declaration of Dr. L. Jay Katz in Support of Glaukos's Opening Claim Construction Brief (Jul. 17, 2014) (78 pages).
Excerpts from the certified Deposition Transcript of Richard A. Hill, M.D., Jul. 17, 2014, pp. 1, 3-4, 240-253, and 270.

(56) References Cited

OTHER PUBLICATIONS

Declaration of Joseph F. Jennings in Support of Glaukos's Opening Claim Construction Brief (Jul. 18, 2014) (78 pages).
Glaukos' Opening Claim Construction Brief (Jul. 18, 2014) (30 pages).
Excerpts from the certified Deposition Transcript of Gregory Smedley, Ph.D., Aug. 6, 2014, pp. 1, 3-4, 6-7, 12, 99-102, 106-114, and 203.
Transcends's Answering Claim Construction Brief (Aug. 15, 2014) (375 pages).
Transcend Medical, Inc.'s Second Supplemental Invalidity Contentions (Aug. 26, 2014) (39 pages).
Glaukos Corporation's Reply Claim Construction Brief (Aug. 29, 2014) (14 pages).
Glaukos Corporation's Responses to Transcend Medical, Inc.'s Fourth Set of Interrogatories (Nos. 14-15) dated Aug. 29, 2014.
Glaukos Corporation's Supplemental Response to Transcend Medical, Inc.'s Interrogatory No. 3 dated Aug. 29, 2014.
Transcend Medical, Inc.'s Responses and Objections to Glaukos Corporation's Fourth Set of Interrogatories, Served Aug. 29, 2014 [Redacted—Public Version].
Transcend Medical, Inc.'s Responses and Objections to Glaukos Corporation's First Set of Requests for Admission, Served Aug. 29, 2014.
Transcend Medical, Inc.'s Redacted Second Amended Complaint for Declaratory Judgment of Patent Non-Infringement, Invalidity and Unenforceability (Sep. 10, 2014) (206 pages).
Transcend Medical, Inc.'s Redacted Exhibit A to the Stipulation and Proposed Order for Second Amended Complaint and Amendment of Scheduling Order (Sep. 11, 2014) (205 pages).
Transcend Medical, Inc.'s Redacted Sur-Reply Claim Construction Brief (Sep. 17, 2014) (14 pages).
Glaukos Corporation's Redacted Answer and Counterclaims to the Second Amended Complaint for Declaratory Judgment (Sep. 29, 2014) (27 pages).
Deposition of Jay Katz, Dated Oct. 1, 2014.
Transcend's Answer to Counterclaims (Oct. 17, 2014) (10 pages).
Glaukos Corporation's Supplemental Disclosures, Served Oct. 29, 2014.
Correspondence from the U.S. Patent and Trademark Office granting the petition to correct inventorship, filed in the prosecution history of U.S. Pat. No. 8,075,511 (dated Oct. 31, 2014).
Markman Hearing Transcript before Honorable Mitchell S. Goldberg, Dated Nov. 13, 2014.
Transcend Medical, Inc.'s Supplemental Disclosures, Served Nov. 14, 2014.
Correspondence from the U.S. Patent and Trademark Office granting the petition to correct inventorship, filed in the prosecution history of U.S. Pat. No. 7,857,782 (dated Nov. 18, 2014).
Transcend's Responses and Objections to Glaukos Corporation's Fifth Set of Interrogatories dated Nov. 20, 2014.
Glaukos Corporation's Responses to Transcend Medical, Inc.'s Sixth Set of Interrogatories (Nos. 20-25) dated Nov. 21, 2014.
Glaukos Corporation's Supplemental Response to Transcend Medical, Inc.'s Third Set of Interrogatories (No. 13) dated Nov. 21, 2014.
Decision of Technical Board of Appeal 3.2.08 of Jan. 15, 2015, submitted in the prosecution history of EP1977724, dated Jan. 15, 2015.
Memorandum Opinion re Claim Construction dated Jan. 16, 2015.
Order re Claim Construction dated Jan. 16, 2015.
Correspondence from the U.S. Patent and Trademark Office granting the petition to correct inventorship, filed in the prosecution history of U.S. Pat. No. 8,579,846 (dated Feb. 10, 2015).
Expert Report of Harold (Hal) J. Walbrink Regarding the Invalidity of Various Claims of the Patents in Suit and the Obviousness of Certain Claim Elements (Mar. 9, 2015) (63 pages).
Expert Report of Richard Lewis, M.D. (Mar. 9, 2015) (79 pages).
Rebuttal Expert Report of Richard Lewis, M.D. (Apr. 24, 2015) (39 pages).
Rebuttal Expert Report of Ron Yamamoto (Apr. 24, 2015) (65 pages).
Rebuttal Expert Report of John Richards (Apr. 24, 2015) (16 pages).
Rebuttal Expert Report of L. Jay Katz MD. (Apr. 24, 2015) (130 pages).
Expert Supplemental Report of Harold (Hal) J. Walbrink Regarding the Invalidity of Various Claims of the Patents-in-suit and the Obviousness of Certain Claim Elements (May 8, 2015) (17 pages).
Excerpts from the certified Deposition Transcript of Ron Yamamoto, dated May 22, 2015.
Excerpts from the certified Deposition Transcript of Joseph Caprioli, M.D., dated May 27, 2015.
Deposition Transcript of M. Bruce Shields dated Jun. 3, 2015 [Redacted—Public Version].
Excerpts from the certified Deposition Transcript of Richard Lewis, M.D., dated Jun. 5, 2015.
Deposition of Jay Katz, Dated Jun. 10, 2015.
Webpage regarding the definition of "subchoroidal" from Merriam Webster's Medical Dictionary, available at: http://www.merriam-webster.com/medical/subchoroidal (last visited Jun. 11, 2015).
Glaukos's Motion for Summary Judgment on Transcend's Third Cause of Action for a Declaratory Judgment of Unenforceability for Inequitable Conduct dated Jun. 12, 2015.
Glaukos's Opening Brief in Support of Glaukos's Motion for Summary Judgment on Transcend's Third Cause of Action for a Declaratory Judgment of Unenforceability for Inequitable Conduct dated Jun. 12, 2015.
Glaukos's Statement of Undisputed Material Fact dated Jun. 12, 2015.
Transcend's Motion for Summary Judgment of Invalidity dated Jun. 12, 2015.
Transcend's Motion for Summary Judgment of Non-Infringement dated Jun. 12, 2015.
Deposition of John Richards, Dated Jun. 17, 2015.
Transcend's Memorandum in Support of Transcend's Motion for Summary Judgment of Invalidity dated Jun. 19, 2015 [Redacted—Public Version].
Transcend's Statement of Undisputed Facts in Support of Transcend's Motion for Summary Judgment of Non-Infringement dated Jun. 19, 2015 [Redacted—Public Version].
Transcend's Statement of Undisputed Facts in Support of Transcend's Motion for Summary Judgment of Invalidity dated Jun. 19, 2015 [Redacted—Public Version].
Transcend's Memorandum in Support of Transcend's Motion for Summary Judgment of Non-Infringement dated Jun. 19, 2015 [Redacted—Public Version].
Declaration of Vasquez in Support of Transcend's Motion for Summary Judgment of Non-Infringement dated Jun. 19, 2015 [Redacted—Public Version].
Declaration of Du Vergier in Support of Transcend's Motion for Summary Judgment of Non-Infringement dated Jun. 19, 2015 [Redacted—Public Version].
Declaration of Alyse Katz in Support of Motion for Summary Judgment of Invalidity dated Jun. 19, 2015 [Redacted—Public Version].
Declaration of Joshua Stowell in Support of Glaukos's Motion for Summary Judgment on Transcend's Third Cause of Action for a Declaratory Judgment of Unenforceability for Inequitable Conduct dated Jun. 19, 2015 [Redacted—Public Version].
Declaration of Richard Lewis M.D. in Support of Glaukos's Oppositions to Transcend's Motions for Summary Judgment of Non-Infringement and Invalidity dated Jul. 2, 2015.
Declaration of Ron Yamamoto in Support of Glaukos's Opposition to Transcend's Motion for Summary Judgment of Invalidity dated Jul. 2, 2015.
Declaration of John Richards in Support of Glaukos's Opposition to Transcend's Motion for Summary Judgment of Invalidity dated Jul. 2, 2015.
Glaukos's Opposition to Transcend's Motion for Summary Judgment of Invalidity dated Jul. 2, 2015.
Transcend's Memorandum in Opposition to Glaukos' Motion for Summary Judgment of No Inequitable Conduct dated Jul. 9, 2015 [Redacted—Public Version].

(56) References Cited

OTHER PUBLICATIONS

Declaration of Julien Du Vergier in Support of Transcend's Opposition to Glaukos' Motion for Summary Judgment of No Inequitable Conduct dated Jul. 9, 2015 [Redacted—Public Version].
Transcend's Response and Statement of Further Undisputed Facts in Support of its Opposition to Glaukos' Motion for Summary Judgment of No Inequitable Conduct dated Jul. 9, 2015 [Redacted—Public Version].
Glaukos's Opposition to Transcend's Motion for Summary Judgment of Non-Infringement dated Jul. 9, 2015 [Redacted—Public Version].
Glaukos's Statement of Material Facts that Present Genuine Issues for Trial in Opposition to Transcend's Motion for Summary Judgment of Non-Infringement dated Jul. 9, 2015 [Redacted—Public Version].
Declaration of L. Jay Katz in Support of Glaukos's Oppositions to Transcend's Motions for Summary Judgment of Non-Infringement and Invalidity dated Jul. 9, 2015 [Redacted—Public Version].
Declaration of Joshua Stowell in Support of Glaukos's Opposition to Transcend's Motion for Summary Judgment of Invalidity dated Jul. 9, 2015 [Redacted—Public Version].
Glaukos's Statement of Material Facts that Present Genuine Issues for Trial in Opposition to Transcend's Motion for Summary Judgment of Invalidity dated Jul. 9, 2015 [Redacted—Public Version].
Declaration of Joseph F. Jennings in Support of Glaukos's Opposition to Transcend's Motion for Summary Judgment of Non-Infringement dated Jul. 9, 2015 [Redacted—Public Version].
Transcend's Reply in Support of its Motion for Summary Judgment of Invalidity dated Jul. 17, 2015 [Redacted—Public Version].
Declaration of Alyse L. Katz in Support of Transcend's Reply in Support of its Motion for Summary Judgment of Invalidity filed Jul. 17, 2015 [Redacted—Public Version].
Transcend's Reply in Support of its Motion for Summary Judgment of Non-Infringement dated Jul. 17, 2015 [Redacted—Public Version].
Declaration of Julien Du Vergier in Support of Transcend's Reply in Support of its Motion for Summary Judgment of Non-Infringement dated Jul. 17, 2015 [Redacted—Public Version].
Glaukos's Reply in Support of its Motion for Summary Judgment on Transcend's Third Cause of Action for a Declaratory Judgment of Unenforceability for Inequitable Conduct dated Jul. 17, 2015 [Redacted—Public Version].
Second Declaration of Joshua Stowell in Support of Glaukos's Motion for Summary Judgment on Transcend's Third Cause of Action for a Declaratory Judgment of Unenforceability for Inequitable Conduct dated Jul. 17, 2015 [Redacted—Public Version].
Transcend's Letter to Judge Regarding Citation Errors and Missing Exhibit Pages in Briefing Papers dated Jul. 28, 2015.
Order Denying Glaukos Corporation's Motion for Summary Judgment Regarding Unenforceability due to Inequitable Conduct, dated Sep. 18, 2015.
Alexander, L., et al., Disistronic Polioviruses as Expression Vectors for Foreign Genes. 1994. Aids Research and Human Retroviruses. vol. 10, Supplement 2, S57-S60.
Bahler, Cindy K., BS, Gregrory T. Smedley, PhD, Jianbo Zhou, PhD, Douglas H. Johnson, MD., *Trabecular Bypass Stents Decrease Intraocular Pressure in Cultured Human Anterior Segments*, American Journal of Ophthalmology, Dec. 2004, vol. 138, pp. 988-994.
Biomedical Foundations of Ophthalmology, vol. 1, Harper & Row Publishers, 1983 pp. 1-74.
Bucciarelli, Patrice D., Working Model is Next Step in Team's Long Journey to Commercial Product, Healthfirst, Business First of Louisville, louisville.bizjournals.com, Feb. 27, 2004.
Coote, "Glaucoma Hollow Fiber Filters—A New Glaucoma Seton. Preliminary Results," J. Glaucoma, vol. 8, No. 1, Supplement (1999), p. S4 (1 page).
Demailly, P., et al., "Non-penetrating deep sclerectomy combined with a collagen implant in primary open-angle glaucoma. Medium-term retrospective results", J. Fr. Ophthalmol., vol. 19, No. 11, 1996, pp. 659-666 (abstract only).

Ellis, R., "Reduction of Intraocular Pressure Using Plastics in Surgery," American Journal of Ophthalmology, vol. 50, pp. 733-743 (1960).
Emi, Kazayuki, et al., Hydrostatic Pressure of the Suprachoroidal Space, Investigative Ophthalmology & Visual Science, vol. 30, No. 2, Feb. 1989 (pp. 233-239).
Gedde, Steven J. et al. Three-year follow-up of the tube versus trabeculectomy study, American Journal of Ophthalmology, vol. 148, No. 5, Nov. 2009.
Green, K. et. al, "Fate of Anterior Chamber Tracers in the Living Rhesus Monkey Eye with Evidence for Uveo-Vortex Outflow," Fourth William Mackenzie Memorial Symposium, 1977, pp. 731-739.
Glaucoma—Basic and Clinical Science Course, Section 10, Chapter 11, 1998-1999, American Academy of Ophthalmology, p. 9.
http://en.wikipeda.org/wiki/5-fluorouracil online encyclopedia entry for 5-fluorouracil. Accessed Nov. 28, 2007.
Haag-Streit Contact Glasses Brochure, retrieved Mar. 20, 2007.
Hamard, P., et al., "Deep nonpenetrating sclerectomy and open angle glaucoma. Intermediate results from the first operated patients", J. Fr. Ophthalmol., vol. 22(j), Feb. 1999, pp. 25-31 (abstract only).
Hill, R.A., Q. Ren, D.C. Nguyen, L.H. Liaw, & M.W. Berns, Free-electron Laser (FEL) Ablation of Ocular Tissues, *Lasers Med Sci 1998*, vol. 13, pp. 219-226.
Hill, Richard A., MD, George Baerveldt, MD, Serdar A. Ozler, MD, Michael Pickford, BA, Glen A. Profeta, BS, & Michael W. Berns, PhD, Laser Trabecular Ablation (LTA), *Lasers in Surgery and Medicine*, 1991, vol. 11, pp. 341-346.
Histology of the Human Eye, An Atlas and Textbook, Chapter Eight: Choroid (1971) (74 pages).
Hoerauf, Hans, Christopher Wirbelauer, Christian Scholz, Ralf Engelhardt, Peter Koch, Horst Laqua, and Reginald Birngruber, *Slit-lamp-adapted optical coherence tomography of the anterior segment*, Graefe's Arch Clin Exp Ophthalmol, 2000, vol. 238, pp. 8-18.
Hoskins, H. Dunbar, et al., Diagnosis and Therapy of the Glaucomas, Chapter 4: Aqueous Humor Outflow, $6_1$ edition, pp. 41-66 (1989) (28 pages).
"Hyaluronan" article, online encyclopedia, section on "Medical Applications" accessed Monday Sep. 27, 2010, http://en.wikipedia.org/wikiHyaluronic_acid.
"Improving the flow: A survey of available implants", EW Practice Management, Oct. 11, 1999, website "http//www.eyeworld.org/tooltime/999inserts.asp".
Jacobi, Phillip C., MD, Thomas S. Dietlein, MD and Gunter K. Krieglstein, MD, Microendoscopic Trabecular Surgery in Glaucoma Management, *Ophthalmology*, 1999 vol. 106, No. 3, pp. 538-544
Jacobi, Phillip C., MD, Thomas S. Dietlein, MD and Gunter K. Krieglstein, MD, Bimanual Trabecular Aspiration in Pseudoexfoliation Glaucoma, *Ophthalmology*, 1998, vol. 105, No. 5, May 1998, pp. 886-894.
Jacobi, Phillip C., MD, Thomas S. Dietlein, MD and Gunter Krieglstein, MD, Goniocurettage for Removing Trabecular Meshwork: Clinical Results of a new Surgial Technique in Advanced Chronic Open-Angle Glaucoma, American Journal of Ophthalmology, May 1999, pp. 505-510.
Johnson, M. C., et al.: The Role of Schlemm's Canal in Aqueous Outflow from the Human Eye; Investigative Ophhalmology; Mar. 1983; vol. 24, pp. 321-325.
Jordon, et al., "A Novel Approach to Suprachoroidal Drainage for the Surgical Treatment of Intractable Glaucoma," J Glaucoma 15(3): 200-205 (2006).
Jens F. Jordan, Thomas S. Dietlein, Sven Dinslage, Christoph Lüke, Walter Konen, Günter K. Krieglstein, *Cyclodialysis ab interno as a surgical approach to intractable glaucoma*, Graefe's Arch Clin Exp Ophthalmol (2007) 245:1071-1076.
Karlen, M. E., et al., "Deep sclerectomy with collagen implant: medium term results", Br. J. Ophthalmol. vol. 83, No. 1, Jan. 1999, pp. 6-11 (abstract only).

(56) References Cited

OTHER PUBLICATIONS

Katuri, Kalyan C., Asrani, Sanjay and Ramasubramanian, Melur K., "Intraocular Pressure Monitoring Sensors", IEEE Sensors Journal, vol. 8, No. 1, Jan. 2008, 8 pp.
Lee et al., "Aqueous-venous Shunt and Intraocular Pressure. Preliminary Report of Animal Studies," Investigative Opthalmology, vol. 5, No. 1 (Feb. 1966), pp. 59-64 (6 pages).
Llobet, et al., Understanding Trabecular Meshwork Physiology: A Key to the Control of Intraocular Pressure?, News Physiol Sci vol. 18, pp. 205-209 (2003).
McAllister, A., et al., Recombinant yellow fever viruses are effective therapeutic vaccines for treatment of murine experimentalsolid tumors and pulmonary metastases. Oct. 2000. Journal of Virology. Vo. 74, No. 19, : 9197-9205, see Fig 1 and pp. 9202-9204.
McGehee, Blake E. et al., "Bilateral Retinal Detachment in a Patient with Vogt-Koyanagi-Harada Syndrome," Emergency Radiology (2005) 11: 366-371.
Miyazaki, Akiko, et al., Postoperative Results of Combined Trabeculotomy, Phacoemulsification and Intraocular Lens Implantation With Self-Sealing Wound, Japanese Journal of Ophthalmic Surgery, 1997, pp. 537-542, vol. 10, No. 4.
Needle gauge comparison chart, wikipedia, Feb. 22, 2016.
Pesin, Michael A. J., Sr., et al., Management of late-onset angle-closure glaucoma associated with retinopathy of prematurity. Ophthamology 98(7): 1991 1093-98.
Portney, G., M.D., "Silicone Elastomer Implantation Cyclodialysis: A Negative Report," Arch. Opthalmol., vol. 89, pp. 10-12 (Jan. 1973).
Ripart et al., Medical Canthus Single-Injection Episcleral (Sub-Tenan Anesthesia): Computed Tomography Imaging. International Ophthalmology 14: 11%124, 1990.
Ritch, et al., "Uveoscleral Outflow," The Glaucomas, 2nd Edition, Chapter 15, pp. 337-343, 1996.
Rizq, et al., Intraocular Pressure Measurement at the Choroid Surface: A Feasibility Study with Implications for Implantable Microsystems, Br J Ophthalmol 2001; 85:868-871, Jul. 2001.
Rosenberg, et al., "Implants in Glaucoma Surgery", The Glaucomas 1996, Chapter 88, pp. 1783-1807 (27 pages).
Rowan, MD, *Combined Cyclodialysis and Cataract Surgery*, Ophthalmic Surgery and Lasers, Dec. 1998, vol. 29, No. 12, pp. 962-968 (9 pages).
Ruffolo, Robert R., Jr.,; Distribution and Function of Peripheral-Adrenoceptors in the Cardiovascular System; Pharm. Biochem and Behavior, 22, 827 (1985).
Saheb et al., Optical Coherence Tomography of the Suprachoroid After CyPass Micro-Stent Implantation for the Treatment of Open-Angle Glaucoma, Br. J. Ophthalmology, 98:19-23 (2014).
Samalonis, Lisa B., "New Horizons in the surgical treatment of glaucoma", EW Glaucoma, Oct. 11, 1999, website "http//www.eyeworld.org/sep99/999p62.asp".
Schwartz, Arthur L., MD, & Douglas R. Anderson, MD, Trabecular Surgery, *Arch Ophthalmol*, vol. 92, Aug. 1974, pp. 134-138.
Sherman, Steven H., et al., "The Fate of Anterior Chamber Fluorescein in the Monkey Eye 1. The Anterior Chamber Outflow Pathways", Exp. Eye Res. vol. 27, pp. 159-173 (1978) (15 pages).
Strange, Kevin (edited by), *Cellular and Molecular Physiology of Cell Volume Regulation*, Library of Congress Cataloging in-Publication Data, CRC Press, Inc., 1994 pp. 312-321.
Timmermans, et al., Possible Subdivion of Postsynapic Adrenoceptors Mediating Pressor Responses in the Pithed Rat; Nauyn-Schmeideberg's Arch. Pharmacol., 310, pp. 189-193 (1979).
Toris, Carol B. Aqueous humor dynamics I. Current topics in membranes. In: Civan, MM (Ed.) The Eye's Aqueous Humor, 62, (2008): 193-229).
Toris, Carol B., Uveoscleral Outflow, Current understanding and methods of measurement, Glaukoma Today, Sep./Oct. 2013, pp. 36-37.
"Transcend Medical CyPass® System—Instructions for Use," (Release date Apr. 29, 2013).

Tripathi, et al., "Functional Anatomy of the Anterior Chamber Angle", Biomedical Foundation of Ophthalmology, vol. 1, Chapter 10,pp. 1-74; edited by Thomas Dune and Edward Jaeger, Revised Edition, 1983,—Harper & Row, Publishers.
Excerpt of Ramesh C. Tripathi & Brenda J. Tripathi, Chapter 1: Anatomy of the Human Eye, Orbit, and Adnexa, in Ramesh C. Tripathi & Brenda J. Tripathi, The Eye (Academic Press, Inc. 1984).
Troncoso, Manuel U., Use of tantalum implants for inducing a permanent hypotony in rabbits' eyes, American Journal of Ophthalmology, vol. 32, No. 4, Apr. 1949, pp. 499-508 (11 pages).
Volk, "Aspheric Ophthalmic Lenses", Refraction, International Ophthalmology Clinics, vol. 5, No. 2, Jun. 1965.
Wagner, Justin A., Edwards, Aurélie, and Schuman, Joel S., Characterization of Uveoscleral Outflow in Enucleated Porcine Eyes Perfused Under Constant Pressure, *Invest Ophthalmol Vis Sci*. Sep. 2004; 45(9): 3203-3206 (9 pages).
Walter, et al., Development of a Completely Encapsulated Intraocular Pressure Sensor, Ophthalmic Research 2000: 32:278-284.
Webster's Third New International Dictionary of the English Language (Unabridged), definitions of "deploy" and "deployment", p. 605 (2002) (4 pages).
Wilson, Ellen D., "Implants offer choices for glaucoma surgeons", EW Glaucoma, Oct. 11, 1999, website "http://www.eyeorld.org/sep99/999p60.asp".
Zhou, Jianbo, PhD, Gregory T. Smedley, PhD., *A Trabecular Bypass Flow Hypothesis*, Feb. 2005, vol. 14 No. 1, pp. 74-83.
Ozdamar, et al., "Suprachoroidal Seton Implantation in Refractory Glaucoma: A novel Surgical Technique", Journal of Glaucoma 12:354-359, 2003.
Tsontcho Ianchulev, Chapter 21: The CyPass Suprachoroidal Micro-Stent, in J.R. Samples & I.I.K. Ahmed (eds.), Surgical Innovations in Glaucoma 229 (Springer Science+Business Media 2014).
Tsontcho Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL. Ophthalmology Oct. 16-19, 2010, Chicago, IL.
Tsontcho Ianchulev, Chapter 3: Suprachoroidal Space as a Therapeutic Target, in J.R. Samples & I.I.K. Ahmed (eds.), Surgical Innovations in Glaucoma 33 (Springer Science+Business Media 2014).
Website entitled, "About Glaukos—History," available at: http://www.glaukos.com/about-glaukos/history (last accessed Jun. 29, 2015).
Office Action in related European application No. 04779911.9, dated Apr. 17, 2009, 4 pp.
U.S. Appl. No. 60/281,973, entitled "Glaucoma Shunt and Methods Thereof for Glaucoma Treatment," to Tu (filed Apr. 17, 2001).
European Extended Search Report in Application No. 15166921.5 dated Dec. 15, 2015.
Office Action in Japanese Application No. 2014-188283 dated on Sep. 4, 2015.
First Office Action in Australian Application No. 2014-201621 dated Mar. 5, 2015.
International Search Report and Written Opinion in PCT/US2011/061967 dated Jun. 28, 2012.
International Search Report and Written Opinion in PCT/US2014/024889 dated Jul. 17, 2014.
International Preliminary Report on Patentability in PCT/US2014/024889 dated Sep. 15, 2015.
Office Action in European Application No. 14717584.8 dated Jul. 15, 2016.
Office Action from the USPTO dated Jun. 28, 2010 and Glaukos's response to that Office Action from the file history of U.S. Pat. No. 8,075,511.
Troncoso, "Cyclodialysis with Insertion of a Metal Implant in the Treatment of Glaucoma".
Gimbel, H.V., et al., "Small incision trabeculotomy combined with phacoemulsificatin and intraocular lens implantation", J Cataract Refract Surg, vol. 19:92-96 (Jan. 1993).
Kampik, Anselm Franz Grehn, Nutzen and Risiken Augenärzticher Therapie, *Hauptreferate der XXXIII, Essener Fortbildung für*

(56) References Cited

OTHER PUBLICATIONS

*Augenärzte*, Dec. 1998. (English translated version enclosed Benefits and Risks of Ophthalmological Therapy).

Alm et al., Uveoscleral Outflow: Biology and Clinical Aspects (Mosby-Wolfe 1998); chapters 1, 3, 6, and 7.

Bron et al., Wolff's Anatomy of the Eye and Orbit, Eighth Ed. (Chapman & Hall Medical 1997) (pp. 223, 226, 337).

Shields, M. Bruce, Aqueous Humor Dynamics, Textbook of Glaucoma, Fourth Ed., Williams & Wilkins Publishers, 1998, Ch. 2, pp. 5-31.

Smit, Barbara A., M.D., Ph.D., et al.; Effects of Viscoelastic Injection into Schlemm's Canal in Primate and Human Eyes; American Academy of Ophthalmology; Apr. 2002; No. 109, No. 4: pp. 786-792.

SHUNT DEVICE AND METHOD FOR TREATING OCULAR DISORDERS

CROSS-REFERENCE TO RELATED APPLICATIONS

This application is a continuation of U.S. patent application Ser. No. 14/316,605, filed Jun. 26, 2014, now U.S. Pat. No. 9,492,320, issued on Nov. 15, 2016, which is a continuation of U.S. patent application Ser. No. 12/966,889, filed Dec. 13, 2010, now U.S. Pat. No. 8,771,217, issued on Jul. 8, 2014, which is a divisional of U.S. patent application Ser. No. 10/987,114, filed Nov. 12, 2004, now U.S. Pat. No. 7,850,637, issued on Dec. 14, 2010, which is a continuation of U.S. patent application Ser. No. 10/445,740, filed May 27, 2003, now U.S. Pat. No. 6,827,700, issued on Dec. 7, 2004, which is a continuation of U.S. patent application Ser. No. 10/242,385, filed Sep. 12, 2002, now U.S. Pat. No. 6,626,858, issued on Sep. 30, 2003, which is a continuation of U.S. patent Ser. No. 09/558,505, filed Apr. 26, 2000, now U.S. Pat. No. 6,450,984, issued on Sep. 17, 2002, which claims the benefit of U.S. Provisional Application No. 60/131,030, filed Apr. 26, 1999.

STATEMENT REGARDING FEDERALLY SPONSORED R&D

The U.S. Government has reserved a nonexclusive, irrevocable, royalty-free license in the invention with power to grant licenses for all governmental purposes.

BACKGROUND OF THE INVENTION

The present invention is generally directed to a surgical treatment for glaucoma, and relates more particularly to a device and method for continuously decompressing elevated intraocular pressure in eyes affected by glaucoma by diverting aqueous humor from the anterior chamber of the eye into Schlemm's canal where post-operative patency can be maintained with an indwelling shunt which can be surgically placed to connect the canal with the anterior chamber.

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of about 25 collecting channels that drain from Schlemm's canal and into the episcleral venous system. In a normal situation, aqueous production is equal to aqueous outflow and intraocular pressure remains fairly constant in the 15 to 21 mmHg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and TOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

When trabeculectomy doesn't successfully lower the eye pressure, the next surgical step often is an aqueous shunt device. An aqueous diversion device of the prior art is a silicone tube that is attached at one end to a plastic (polypropylene or other synthetic) plate. With an aqueous shunt device, an incision is made in the conjunctiva, exposing the sclera. The plastic plate is sewn to the surface of the eye posteriorly, usually over the equator. A full thickness hole is made into the eye at the limbus, usually with a needle. The tube is inserted into the eye through this hole. The external portion of the tube is covered with either donor sclera or pericardium. The conjunctiva is replaced and the incision is closed tightly.

With prior art aqueous diversion devices, aqueous drains out of the eye through the silicone tube to the surface of the eye. Deeper orbital tissues then absorb the fluid. The outside end of the tube is protected from fibroblasts and scarring by the plastic plate. Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. Many physicians tie an absorbable suture around the tube and wait for the suture to dissolve post-operatively at which time enough scar tissue has hopefully formed around the plate. Some devices contain a pressure-sensitive valve within the tube, although these valves may not function properly. The surgery involves operating in the posterior orbit and many patients develop an eye muscle imbalance and double vision post-operatively. With prior art aqueous shunt devices, a pathway is created for bacteria to get into the eye and endophthalmitis can potentially occur.

The prior art includes a number of such aqueous shunt devices, such as U.S. Pat. No. 4,936,825 (providing a tubular shunt from the anterior chamber to the corneal surface for the treatment of glaucoma), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (generally teaching shunting from the anterior chamber to the scleral or conjunctival spaces).

In addition to the prior art aqueous shunt devices described above, other prior art devices for glaucoma surgery have used setons, or other porous, wick-like components to divert and convey excess aqueous from the anterior chamber to the exterior ocular surface. Examples include U.S. Pat. Nos. 4,634,418 and 4,787,885 (teaching the surgical treatment of glaucoma using an implant that consists of a triangular seton (wick)), and U.S. Pat. No. 4,946,436, (teaching the use of a porous device to shunt anterior chamber to subscleral space). These patents do not teach placement in Schlemm's canal.

Some prior art references for glaucoma management have been directed at Schlemm's canal, but these have not involved the placement of long-term, indwelling shunts. U.S. Pat. No. 5,360,399 teaches the temporary placement of a plastic or steel tube with preformed curvature in Schlemm's canal with injection of a viscous material through the tube to hydraulically expand and hydrodissect the trabecular meshwork. The tube is removed from the canal following injection. Because the tube is directed outwardly from the eye for injection access, the intersection of the outflow element with the preformed curved element within Schlemm's canal is at about a 90 degree angle relative to the plane of the curvature, and 180 degrees away from the anterior chamber. Therefore, at no time does any portion of the '399 device communicate with the anterior chamber. Furthermore, relative to that portion within Schlemm's canal, this tube has a larger diameter injection cuff element, which serves as an adapter for irrigation. Therefore, this device is not adapted for shunting aqueous between the anterior chamber and Schlemm's canal.

Most of the problems that have developed with current glaucoma treatment devices and procedures have occurred because aqueous fluid is drained from inside of the eye to the surface of the eye. A need exists, then, for a more physiologic system to enhance the drainage of aqueous fluid from the anterior chamber into Schlemm's canal. In the vast majority of glaucoma patients, the resistance problem lies between Schlemm's canal and the anterior chamber. The canal itself, the collecting channels and the episcleral venous system all are intact. Enhancing aqueous flow directly into Schlemm's canal would minimize the scarring that usually occurs with external filtration procedure since the internal angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

SUMMARY OF THE INVENTION

The present invention is directed to a novel shunt and an associated surgical method for the treatment of glaucoma in which the shunt is placed to divert aqueous humor from the anterior chamber of the eye into Schlemm's canal. The present invention therefore facilitates the normal physiologic pathway for drainage of aqueous humor from the anterior chamber, rather than shunting to the sclera or another anatomic site as is done in most prior art shunt devices. The present invention is further directed to providing a permanent, indwelling shunt to provide increased egress of aqueous humor from the anterior chamber to Schlemm's canal for glaucoma management.

DETAILED DESCRIPTION OF THE PREFERRED EMBODIMENTS

Figure 1A:
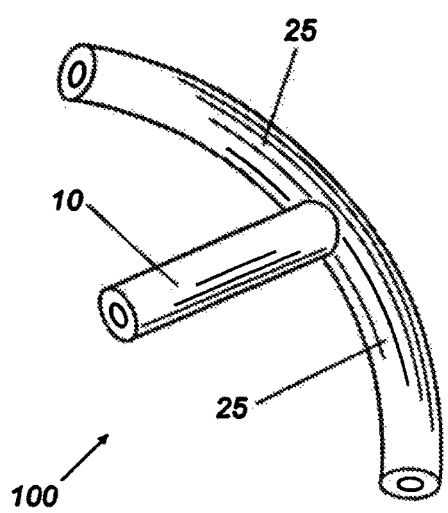
FIG. 1A is an illustration showing an overhead perspective view of one embodiment of the present invention, in which the inventive shunt is comprised of tubular elements extending bi-directionally within Schlemm's canal.

The present invention provides an aqueous humor shunt device to divert aqueous humor in the eye from the anterior chamber into Schlemm's canal, in which the shunt device comprises a distal portion having at least one terminal aspect sized and shaped to be circumferentially received within a portion of Schlemm's canal, and a proximal portion having at least one terminal aspect sized and shaped to be received within the anterior chamber of the eye, wherein the device permits fluid communication between the proximal portion in the anterior chamber to the distal portion in Schlemm's canal. Fluid communication can be facilitated by an aqueous humor directing channel in either the proximal or distal portions, as described below. Fluid communication can also be facilitated by a wicking function of a solid proximal or distal portions of the device, for example.

The present invention also provides embodiments of an inventive shunt comprising a body of biocompatible material of a size and shape adapted to be at least partially circumferentially received within a portion of Schlemm's canal to divert aqueous humor from the anterior chamber of the human eye to and within Schlemm's canal, and wherein the body facilitates the passage of aqueous humor from the anterior chamber into Schlemm's canal. This embodiment of the device of the present invention can be produced without the proximal portion of the previous embodiment extending into the anterior chamber. An aqueous humor directing channel can facilitate the passage of aqueous humor from the anterior chamber into Schlemm's canal. Fluid communication can also be facilitated by a wicking function of a solid body portion, for example.

The invention contemplates many different configurations for an aqueous humor directing channel, provided that each assists in channeling aqueous humor from the anterior chamber to Schlemm's canal, such as by providing a lumen, trough, wick or capillary action. For example, the aqueous humor directing channel can be a fully enclosed lumen, a partially enclosed lumen, or a trough-like channel that is at least partially open. The invention contemplates that a solid monofilament or braided polymer, such as proline, can be inserted into Schlemm's canal to provide a wicking function to facilitate the passage of aqueous humor from the anterior chamber to Schlemm's canal. Such a wicking extension can also be grooved or fluted along any portion of the length thereof, so as to be multi-angular or star-shaped in cross-section. The devices of the present invention can be constructed of a solid, matrix, mesh, fenestrated, or porous material, or combinations thereof.

Traditional glaucoma teaching states that Schlemm's canal in an adult is divided by septa into separate canals, rendering the complete passage of a suture impossible. Preliminary studies on adult human eye bank eyes have shown that Schlemm's canal is, indeed, patent. A suture can be passed through the entire circumference of the canal. It has not been heretofore determined that Schlemm's canal is patent throughout its circumference in normal adult individuals, as opposed to being divided by septae into multiple dead end canals. The invention utilizes this knowledge to access Schlemm's canal and to create and maintain the natural physiologic egress of aqueous humor from the anterior chamber to Schlemm's canal and to the collecting channels.

The present invention also provides methods of use of the shunt devices. One embodiment of the present invention is directed to a surgical method to divert aqueous humor from the anterior chamber of the eye into Schlemm's canal with a device that is implanted to extend from within the anterior chamber to Schlemm's canal. The portion of the device extending into Schlemm's canal can be fashioned from a flexible material capable of being received within a portion of the radius, curvature, and diameter of Schlemm's canal. All or parts of the device may be solid, porous, tubular, trough-like, fenestrated, or pre-curved.

Figure 1B:
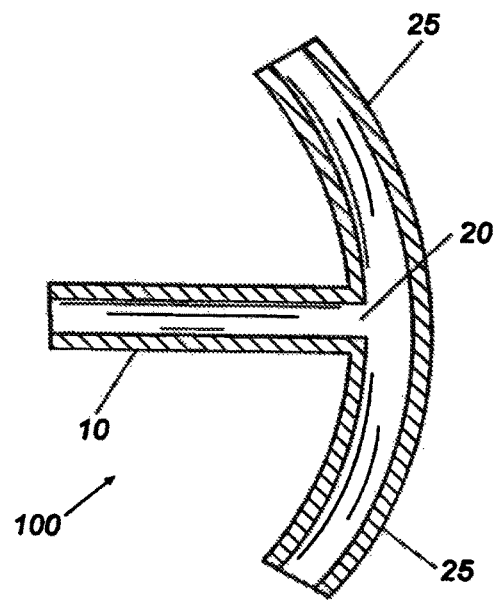
FIG. 1B is an overhead view of the embodiment of the present invention shown in FIG. 1A, with phantom lines detailing the internal communication between the lumens of the tubular elements comprising the inventive device.

One embodiment of the present invention is illustrated in FIG. 1A, in which the shunt device 100 is shown in a side view. The shunt device 100 of this embodiment is comprised of two portions, a proximal portion 10 which joins a distal portion 25. The proximal portion 10 and distal portion 25 shown create an enclosed tubular channeling structure. The total length of the distal portion 25 may be between about 1 and 40 mm, preferably about 6 mm. The same embodiment of the present invention is illustrated with phantom lines showing the internal fluid communication path in FIG. 1B. The lumen or channeling space defined by the walls of the proximal portion 10 and the distal portion(s) 25 are continuous at their junction at the distal portion portal 20.

Figure 1C:
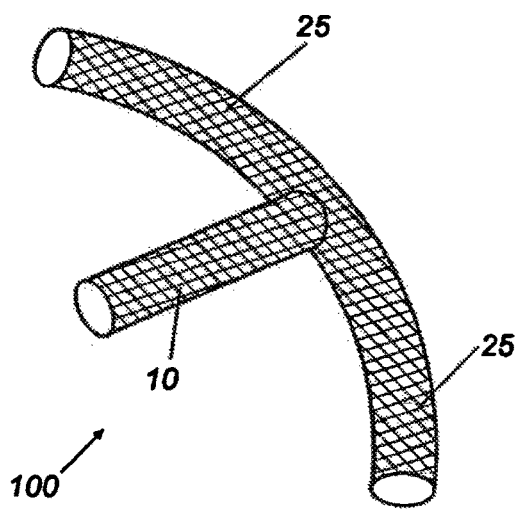
FIG. 1C is an illustration showing an overhead perspective view of one embodiment of the present invention, in which the inventive shunt is comprised of mesh tubular elements extending bi-directionally within Schlemm's canal.
Figure 1D:
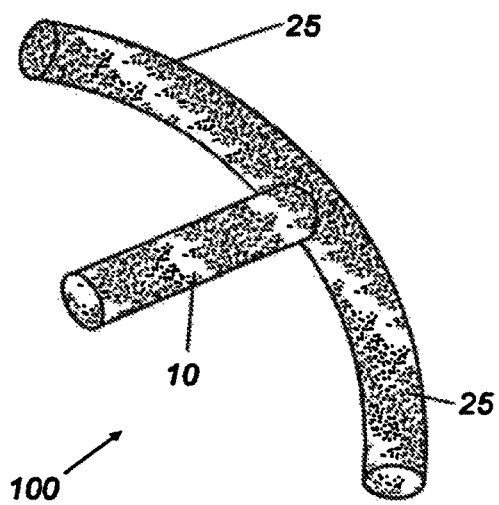
FIG. 1D is an illustration showing an overhead perspective view of one embodiment of the present invention, in which the inventive shunt is comprised of solid, porous elements extending bi-directionally within Schlemm's canal.

An alternate embodiment of the present invention is shown in FIG. 1C, in which the shunt device 100 is comprised of two luminal mesh elements, with a proximal portion 10 which joins a distal portion 25. Yet another embodiment of the present invention is shown in FIG. 1D, in which the shunt device 100 is comprised of two solid, porous elements which may provide wick-like fluid communication therethrough, with a proximal portion 10 which joins a distal portion 25.

Figure 1E:
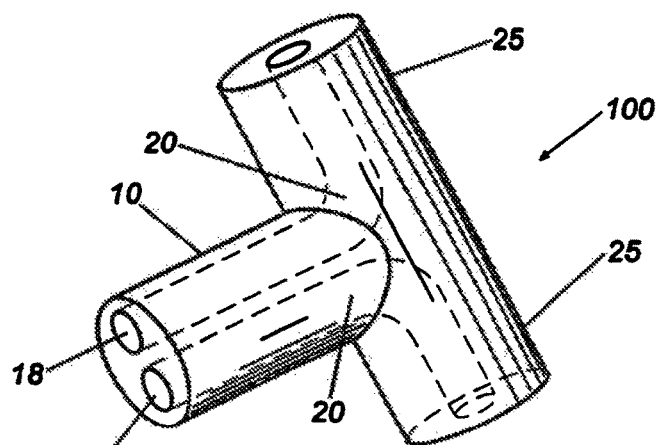
FIG. 1E is an overhead perspective view of another embodiment of the present invention, with phantom lines detailing the internal communication between the two proximal lumens and the single distal lumen of the inventive device.

An alternate embodiment of the present invention is shown in FIG. 1E, in which the shunt device 100 is comprised of a proximal portion 10 having two lumens therein terminating in proximal portion portals 18. The distal portion 25 shaped and sized to be received within Schlemm's canal extends in either direction having separate lumens traversing therethrough from each of the distal portion portals 20.

Figure 2:
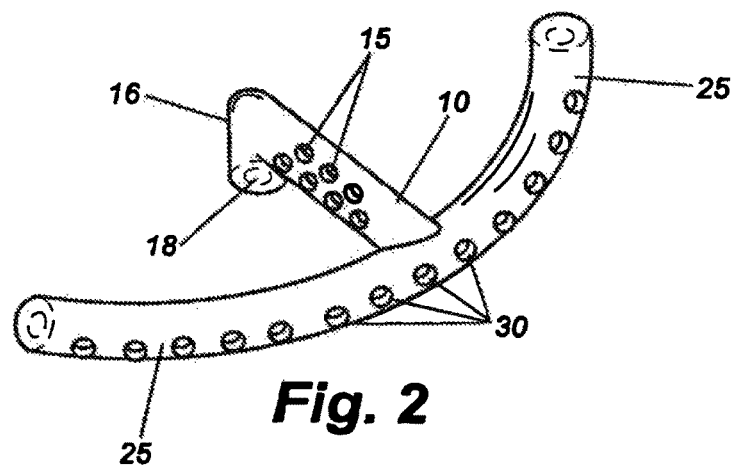
FIG. 2 is an illustration showing another embodiment of the present invention, in which the inventive shunt is comprised of perforated tubular elements and with an angulated terminal aspect of the proximal portion.

Other examples of embodiments of the present invention are shown in FIGS. 2-5D. FIG. 2 shows an embodiment of the inventive shunt in which the device 100 is tubular and fenestrated (15, 30) in its configuration, with an acute (<90°) angle of junction between the proximal portion 10 and the plane defined by the distal portion 25. Such fenestrations (15, 30) may be placed along any portion of the device 100 to facilitate the passage of fluid therethrough, but are particularly directed towards the collecting channels of the eye. FIG. 2 further shows an alternate embodiment of the present invention in which the terminal aspect 16 of the proximal portion is angulated toward the iris 40 with respect to the main axis of the proximal portion 10, with the portal 18 of the proximal portion directed toward the iris 40. In alternate embodiments as shown in FIG. 6C, the portal 18 of the proximal portion 16 is directed away from the iris 40.

Figure 3A:
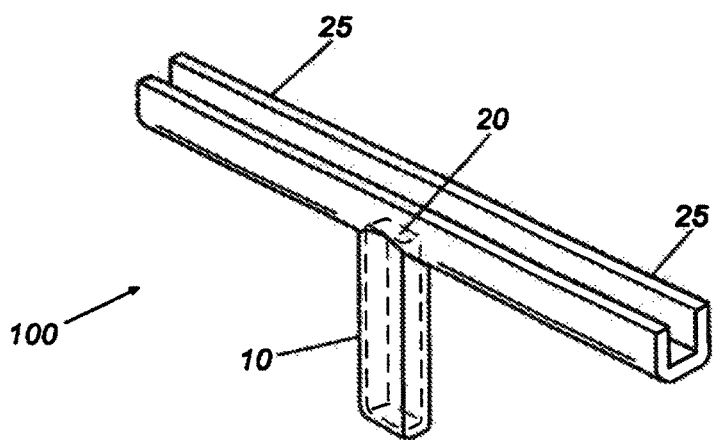
FIG. 3A is an illustration showing a perspective of another embodiment of the present invention in which the inventive shunt is comprised of elements that are partially tubular and partially open in their configuration.

FIG. 3A shows an embodiment of the inventive shunt in which a portion of the channeling device is enclosed and tubular in configuration at the junction of the proximal portion 10 and the distal portion 25, but where the distal portion 10 is a trough-like channel. The distal portion portal 20 is also shown. The invention contemplates that any portion of the device 100 can be semi-tubular, open and trough-like, or a wick-like extension. Tubular channels can be round, ovoid, or any other enclosed geometry. Preferably the non-tubular trough-like aspects are oriented posteriorly on the outer wall of the canal to facilitate aqueous humor drainage to the collecting channels of the eye, as shown in FIG. 3A.

Figure 3B:
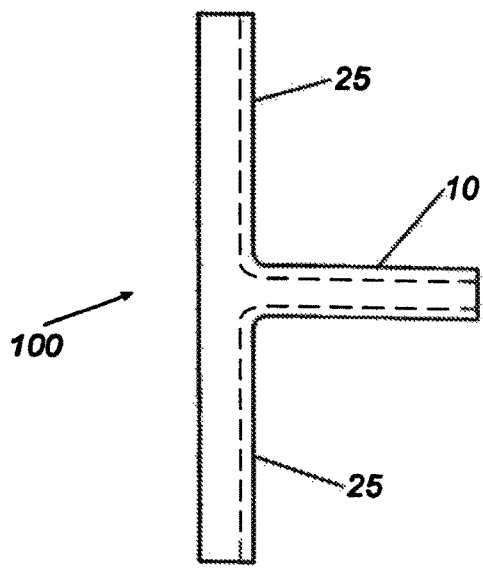
FIG. 3B is an illustration showing a top view of the embodiment of the present invention in FIG. 3A, with phantom lines detailing the internal communication of the device.
Figure 3C:
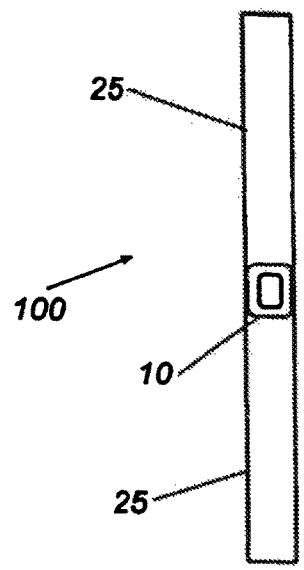
FIG. 3C is an illustration showing a side view from the proximal end of the embodiment of the present invention in FIG. 3A.

FIG. 3B shows an overhead view of the embodiment of the inventive shunt of FIG. 3A, further detailing the relationship among the proximal portion 10 and the distal portion 25. The aqueous humor directing channel is shown in dashed lines. FIG. 3C shows a proximal view of the embodiment of the inventive shunt of FIG. 3A, further detailing the relationship among the proximal portion 10 and the distal portion 25.

Figure 3D:
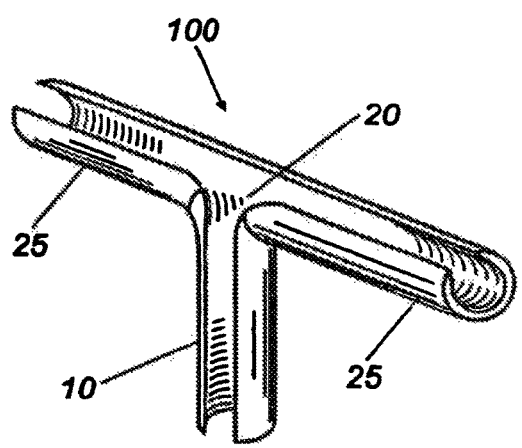
FIG. 3D is an illustration showing a perspective of another embodiment of the present invention in which the inventive shunt is comprised of elements that are partially open and trough-like in their configuration.

FIG. 3D shows another embodiment of the inventive shunt in which the structure of the device 100 comprises an aqueous humor directing channel that is both open and curved in a continuous trough-like configuration along the proximal portion 10 and the distal portion 25. The distal portion portal 20 is also an open trough-like channel.

Figure 4:
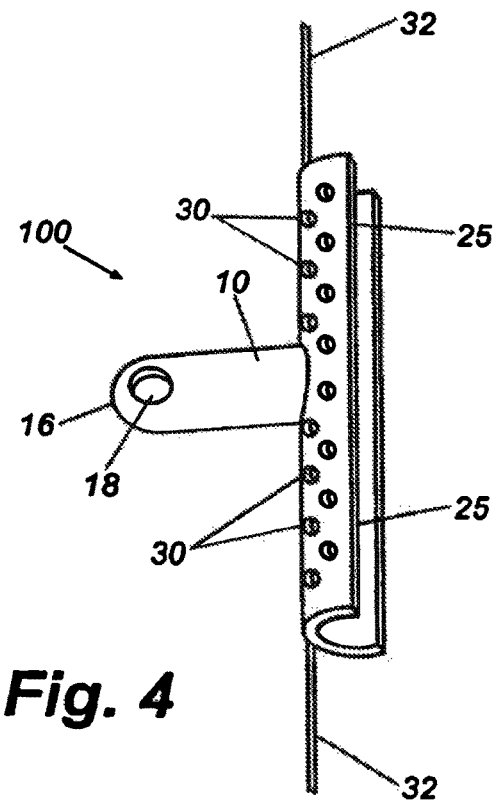
FIG. 4 is an illustration showing another embodiment of the present invention, in which the inventive shunt is comprised of distal elements having wicking extensions at their terminal ends, and in which the proximal portion has a sealed, blunted tip with a portal continuous with the lumen of the proximal portion, oriented to face away from the iris when the device is implanted in Schlemm's canal.

FIG. 4 shows another embodiment of the inventive shunt with the addition of aqueous humor-wicking extensions 32 which are either continuous with, or attached to the terminal aspects of the distal portion 25. The wicking extensions 32 can be fashioned from a monofilament or braided polymer, such as proline, and preferably have a length of 1.0 mm to 16.0 mm. Furthermore, the proximal portion 10 is curved with a sealed, blunted tip 16 and contains a portal 18 in fluid communication with the lumen of the proximal portion and oriented to face away from the iris when the shunt device 100 is implanted in its intended anatomic position. The shunt device 100 can also help to maintain the patency of Schlemm's canal in a stenting fashion.

Figure 5A:
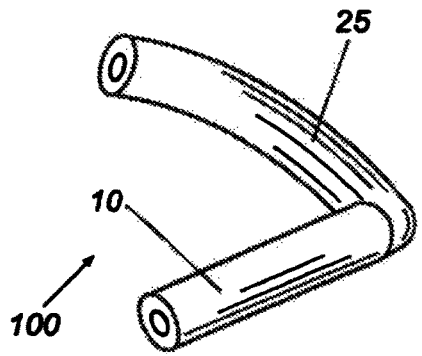
FIG. 5A is an illustration showing another embodiment of the inventive shunt in which a portion of the device enters Schlemm's canal in only one direction and shunts fluid in a non-linear path from the anterior chamber.

FIG. 5A shows another embodiment of the inventive shunt in which the proximal portion 10 joins a single, curved distal portion 25 in a "V-shaped," tubular configuration. The embodiment shown in FIG. 5A can also have a portal (not shown) in the distal portion 25 adjacent to the junction with the proximal portion 10 in order to facilitate bi-directional flow of fluid within the canal. Fenestrations and non-tubular, trough-like terminal openings are contemplated in all embodiments of the invention, and these fenestrations and openings may be round, ovoid, or other shapes as needed for optimum aqueous humor channeling function within the anatomic spaces involved.

Figure 5B:
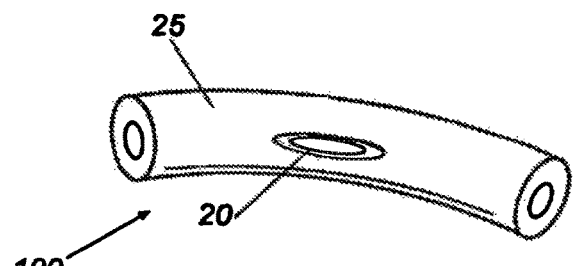
FIG. 5B is an illustration showing an alternative embodiment of the inventive shunt in which the entire shunt is placed within Schlemm's canal but contains a fenestration to maintain fluid egress of aqueous humor from the anterior chamber to Schlemm's canal.

FIG. 5B shows another embodiment of the inventive shunt in which the body or device 100 comprises only a single, curved distal portion 25 which contains a distal portion portal 20 oriented towards the anterior chamber to allow egress of aqueous humor from the anterior chamber to Schlemm's canal. The body of this device can have a length of about 1.0 mm to 40 mm, preferably about 6 mm. The external diameter can be about 0.1 mm to 0.5 mm, or about 0.3 mm.

Figure 5C:
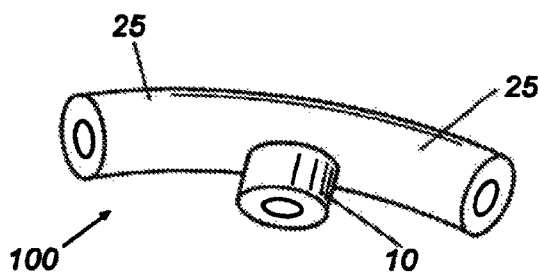
FIG. 5C is an illustration showing a side view of one embodiment of the present invention, in which the inventive shunt is comprised of tubular elements, with a proximal portion extending towards the anterior chamber that is shorter relative to the distal portions which extend bi-directionally within Schlemm's canal.

FIG. 5C shows another embodiment of the inventive shunt in which the device 100 comprises a bi-directional tubular distal portion 25 which is intersected by a proximal portion 10 which is short in length relative to the distal portion 25 and is directed towards the anterior chamber.

Figure 5E:
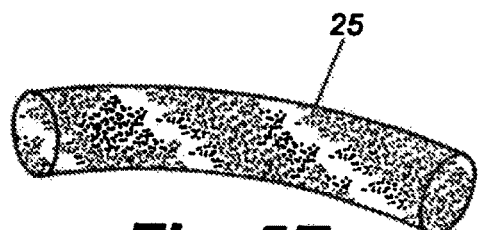
FIG. 5E is an illustration showing an alternative embodiment of the inventive shunt comprised of a solid, but porous wick-like element which is placed within Schlemm's canal.
Figure 5D:
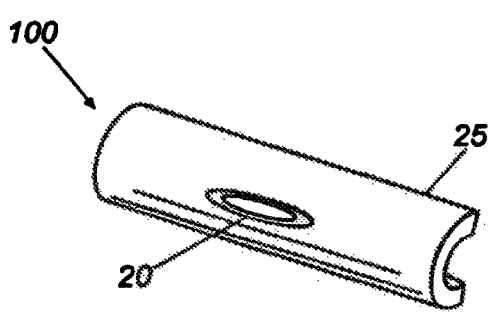
FIG. 5D is an illustration showing an alternative embodiment of the inventive shunt comprised of a partially open trough-like element which is placed within Schlemm's canal but contains a portal to maintain fluid egress of aqueous humor from the anterior chamber to Schlemm's canal.

FIG. 5D shows still another embodiment of the inventive shunt in which the device 100 comprises a bi-directional, trough-like, curved distal portion 25 for insertion into Schlemm's canal, which contains a distal portion portal 20 oriented to allow egress of aqueous humor from the anterior chamber, wherein the trough-like distal portion 25 is oriented to open toward the collecting channels to facilitate the egress of aqueous humor.

FIG. 5E shows another embodiment of the inventive shunt in which the device 100 comprises a bi-directional, solid distal portion 25 for insertion into Schlemm's canal to facilitate the egress of aqueous humor from the canal to the collecting channels in a wicking capacity. The solid distal portion 25 can be porous or non-porous.

As the inventive device is an implant, it can be fabricated from a material that will be compatible with the tissues and fluids with which it is in contact. It is preferable that the device not be absorbed, corroded, or otherwise structurally compromised during its in situ tenure. Moreover, it is equally important that the eye tissues and the aqueous remain non-detrimentally affected by the presence of the implanted device. A number of materials are available to meet the engineering and medical specifications for the shunts. In the exemplary embodiments of the present invention, the shunt device 100 is constructed of a biologically inert, flexible material such as silicone or similar polymers. Alternate materials might include, but are not limited to, thin-walled Teflon, polypropylene, other polymers or plastics, metals, or some combination of these materials. The shunt device 100 may be constructed as either porous or solid in alternate embodiments. The material can contain a therapeutic agent deliverable to the adjacent tissues.

In the embodiments shown in FIGS. 1-4, the proximal portion 10 joins the distal portion(s) 25 at an angle sufficient to allow the placement of the proximal portion 15 within the anterior chamber of the eye when the distal portion 25 is oriented in the plane of Schlemm's canal. The proximal portion 10 is preferably of sufficient length, about 0.1 to 3.0 mm or about 2.0 mm, to extend from its junction with the distal portion 25 in Schlemm's canal towards the adjacent space of the anterior chamber. While many geometries can be used for channeling aqueous humor, the diameter or width of the proximal portion 10 can be sized to yield an internal diameter of between about 0.1 and 0.5 mm, preferably 0.20 mm, for a tubular or curved shunt, or a comparable maximal width for a shunt with a multiangular configuration. In other embodiments, the proximal portion is a non-luminal, non-trough-like wicking extension that provides an aqueous humor directing channel along the length thereof.

Because the nature of the iris 40 is such that it tends to comprise a plurality of rather flaccid fimbriae of tissue, it is desirable to avoid said fimbriae from being drawn into the lumen of an implant, thus occluding the shunt device. Therefore, the proximal portion 10 may contain a plurality of fenestrations to allow fluid ingress, arranged to prevent occlusion by the adjacent iris. Alternately, the proximal portion 10 may comprise only a proximal portion portal 18 in the form of a fenestration oriented anteriorly to provide continuous fluid egress between the anterior chamber of the eye and the directing channel of the shunt. Said fenestrations may be any functional size, and circular or non-circular in various embodiments of the present invention. In addition, a porous structural material can assist in channeling aqueous humor, while minimizing the potential for intake of fimbriae.

Furthermore, the proximal portion 10 may be positioned sufficiently remote from the iris 40 to prevent interference therewith such as by traversing a more anterior aspect of the trabecular meshwork into the peripheral corneal tissue. In yet another possible embodiment, as shown in FIG. 6C, the device 100 may comprise a proximal portion 10 in which the terminal aspect of said proximal portion 10 is curved or angled toward the iris 40, and with a, blunted, sealed tip 16 and a portal 18 oriented anteriorly to face away from the underlying iris 40. Such a configuration would tend to decrease the possibility of occlusion of the shunt device by the iris 40.

The device 100 may contain one or more unidirectional valves to prevent backflow into the anterior chamber from Schlemm's canal. The internal lumen for an enclosed portion of the device or the internal channel defined by the edges of an open portion of the device communicates directly with the inner lumen or channel of the distal portion at the proximal portion portal 20.

The distal portion 25 may have a pre-formed curve to approximate the 6.0 mm radius of Schlemm's canal in a human eye. Such a pre-formed curvature is not required when flexible material is used to construct the shunt device 100. The distal portion 25 may be of sufficient length to extend from the junction with the proximal portion 10 through any length of the entire circumference of Schlemm's canal. Embodiments having a distal portion 25 that extends in either direction within Schlemm's canal can extend in each direction about 1.0 mm to 20 mm, or about 3.0 mm, to permit circumferential placement through Schlemm's canal. The diameter or width of the distal portion 25 can be sized to yield an outer diameter of between about 0.1 and 0.5 mm, or about 0.3 mm, for a tubular or curved shunt, or a comparable maximal width for a shunt with a multiangular configuration. The distal portion 25 may contain a plurality of fenestrations to allow fluid egress, arranged to prevent occlusion by the adjacent walls of Schlemm's canal. In other embodiments, the distal portion is a non-luminal, non-trough-like wicking extension that provides an aqueous humor directing channel along the length thereof.

In the exemplary embodiments of the present invention, the shunt device may be either bi-directional, with the distal portion of the implant intersecting with the proximal portion in a "T-shaped" junction as shown in FIGS. 1A-1E, 2, 3A-3D, 4 and 5C, or uni-directional, with a "V-shaped" junction of the proximal and distal shunt portions, as shown in FIG. 5A. A bi-directional shunt device can have a distal portion that is threaded into opposing directions within Schlemm's canal. In the case of the uni-directional shunt, only the distal shunt portion is placed within Schlemm's canal. In these exemplary embodiments, "non-linear fluid communication" means that at least some portion of the shunt through which fluid passes is not in a straight line. Examples of non-linear shunts are the above described bi-directional "T" shapes, and the uni-directional "V" shapes, or shunts having two channel openings which are not in straight alignment with each other.

Figure 6A:
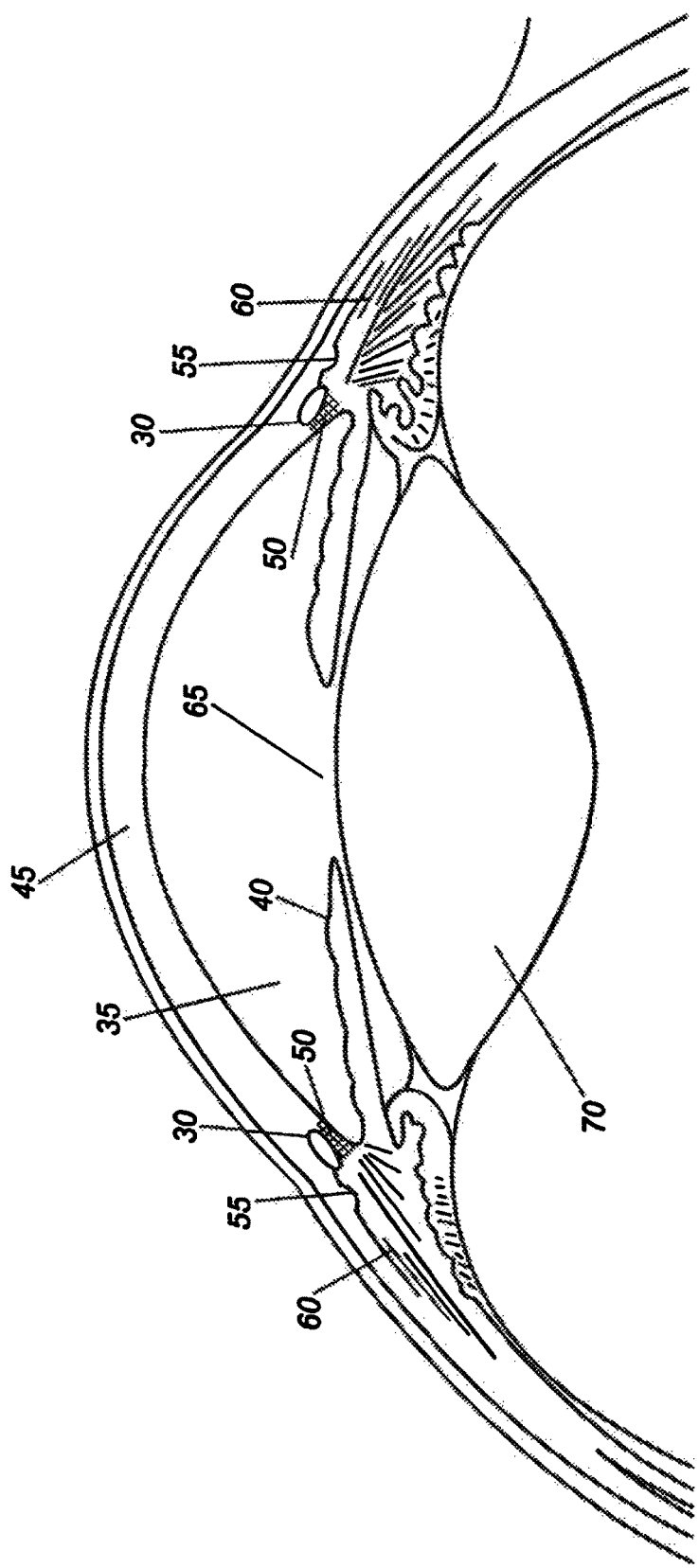
FIG. 6A is an illustration showing certain anatomic details of the human eye.
Figure 6B:
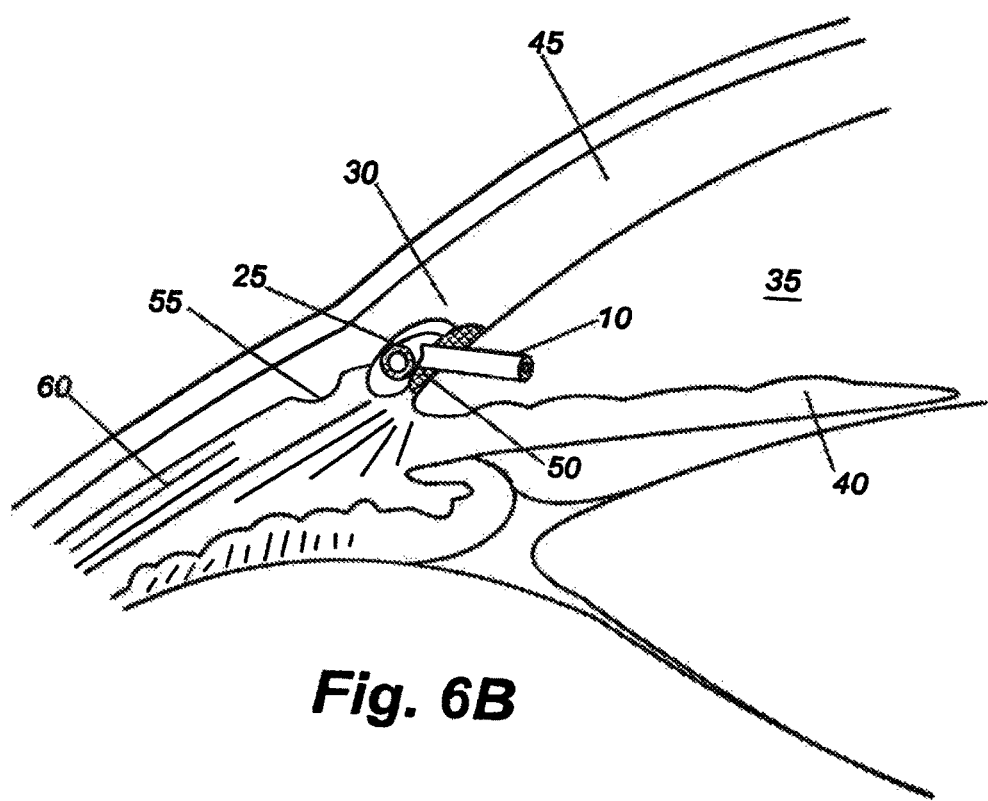
FIG. 6B is a cross-sectional illustration showing the anatomic relationships of the surgical placement of an exemplary embodiment of the present invention.
Figure 6C:
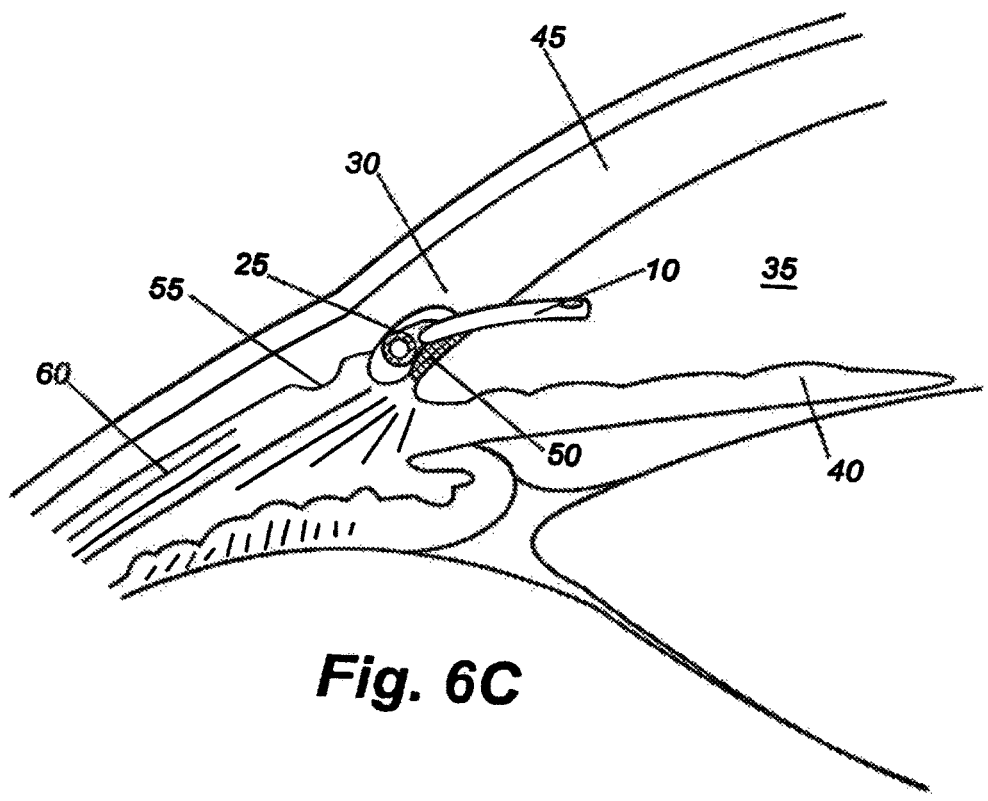
FIG. 6C is a cross-sectional illustration showing the anatomic relationships of the surgical placement of another exemplary embodiment of the present invention in which the proximal portion has an angulated terminal aspect with a sealed, blunted tip with a portal continuous with the lumen of the proximal portion, oriented to face away from the iris when the device is implanted in Schlemm's canal.

The surgical anatomy relevant to the present invention is illustrated in FIG. 6A. Generally, FIG. 6A shows the anterior chamber 35, Schlemm's canal 30, the iris 40, cornea 45, trabecular meshwork 50, collecting channels 55, episcleral veins 60, pupil 65, and lens 70. FIG. 6B illustrates the surgical placement of the exemplary embodiment of the present invention, with the relevant anatomic relationships. It should be noted that the inventive device is designed so that placement of the distal portion 25 within Schlemm's canal 30 results in an orientation of the proximal portion 10 within the anterior chamber 35 within the angle defined by the iris 40 and the inner surface of the cornea 45. Therefore, if the plane defined by Schlemm's canal is defined as zero degrees, the proximal portion 10 can extend therefrom at an angle of between about +60 degrees towards the cornea 45 or −30 degrees toward the iris 40, more preferably in the range of 0 to +45 degrees. This range may vary in individuals having a slightly different location of Schlemm's canal 30 relative to the limbal angle of the anterior chamber 35.

In yet another embodiment of the present invention not shown, the shunt device 100 is configured with one distal portion 25 which is tubular to provide a shunting functionality and a plurality of proximal portions 10 which provide an anchoring function to stabilize the overall implant device, in addition to providing fluid communication from the anterior chamber to Schlemm's Canal.

The surgical procedure necessary to insert the device requires an approach through a conjunctival flap. A partial thickness scleral flap is then created and dissected half-thickness into clear cornea. The posterior aspect of Schlemm's canal is identified and the canal is entered posteriorly. The anterior chamber may be deepened with injection of a viscoelastic and a miotic agent. The proximal portion of the shunt is then inserted through the inner wall of Schlemm's canal and trabecular meshwork into the anterior chamber within the angle between the iris and the cornea. In some cases, as incision may be needed from Schlemm's canal through the trabecular meshwork into the anterior chamber to facilitate passage of the proximal portion therethrough. One arm of the distal portion of the shunt device is grasped and threaded into Schlemm's canal. In a similar fashion, the other arm of the distal portion of the shunt device (when present) is inserted into Schlemm's canal in the opposing direction from the first. The scleral flap and conjunctival wound are closed in a conventional manner.

While the above-described embodiments are exemplary, the invention contemplates a wide variety of shapes and configurations of the shunt to provide fluid communication between the anterior chamber and Schlemm's canal. The above-described embodiments are therefore not intended to be limiting to the scope of the claims and equivalents thereof.

What is claimed is:

1. An ocular implant configured to maintain patency of Schlemm's canal in a stenting fashion, the ocular implant comprising:
    a body of biocompatible material of a size and shape adapted to be at least partially circumferentially retained within a portion of Schlemm's canal,
    wherein the body is non-tubular,
    wherein the body is curved, and
    wherein the body comprises at least one opening along its length configured to facilitate passage of aqueous humor.

2. The ocular implant of claim 1, wherein a portion of the body is oriented to be positioned in the anterior chamber after implantation.

3. The ocular implant of claim 1, wherein the body is shaped to facilitate flow of aqueous humor from Schlemm's canal into one or more collecting channels.

4. The ocular implant of claim 1, wherein the body is elongate and comprises multiple ovoid openings along its length.

5. An implant designed to relieve excessive intraocular pressure, the implant comprising:
    a flexible, elongate body of biocompatible material for implantation in a living human eye comprising a curved channel shaped to be at least partially positioned within a circumferential length of Schlemm's canal;
    wherein the channel is at least partially open along its length to facilitate flow of aqueous humor from Schlemm's canal into one or more collecting channels;
    the channel further having one or more portals oriented to allow flow of aqueous humor from an anterior chamber of the eye into Schlemm's canal.

6. The implant of claim 5, wherein the channel has a trough-like shape to provide stenting support for the patency of Schlemm's canal.

7. The implant of claim 5, wherein the channel includes multiple portals along its length.

8. The implant of claim 7, wherein at least some of the portals are ovoid in shape.

9. The implant of claim 5, wherein a distal portion of the elongate body comprises the curved channel, and wherein the elongate body further comprises a proximal portion that is oriented to be positioned at least partially in the anterior chamber after implantation.

10. The implant of claim 9, wherein the proximal portion is at least partially open to receive aqueous humor from the anterior chamber, and wherein the proximal portion is in fluid communication with the distal portion to facilitate flow of aqueous humor into Schlemm's canal.

11. The implant of claim 5, wherein the biocompatible material comprises metal.

12. The implant of claim 5, wherein a distal end of the body is non-tubular.

13. The implant of claim 5, wherein the opening along the length of the channel is oriented toward one or more of the collecting channels when located within Schlemm's canal.

14. The implant of claim 5, wherein the opening along the length of the channel extends to a distal end of the body.

15. The implant of claim 5, wherein the channel is open along a length that extends to a distal end of the body.

16. An implant designed to relieve excessive intraocular pressure, the implant comprising:
a body of biocompatible material for implantation in a living human eye, wherein the body has a non-linear shape before insertion into the eye;
the body comprising a channel shaped to be at least partially positioned within a circumferential length of Schlemm's canal;
wherein the channel is at least partially open along its length and oriented to facilitate flow of aqueous humor from Schlemm's canal into one or more collecting channels.

17. The implant of claim 16, wherein a distal portion of the body comprises the channel, and wherein the body further comprises a proximal portion that is oriented to be positioned at least partially in an anterior chamber of the eye after implantation.

18. The implant of claim 17, wherein the proximal portion comprises an opening to receive aqueous humor from the anterior chamber, and wherein the proximal portion is in fluid communication with the distal portion to facilitate flow of aqueous humor into Schlemm's canal.

19. The implant of claim 18, wherein the proximal portion is shorter in length than the distal portion.

20. The implant of claim 16, wherein the biocompatible material comprises metal.

21. The implant of claim 16, wherein a distal end of the body is non-tubular.

22. The implant of claim 16, wherein the opening along the length of the channel extends to a distal end of the body.

23. The implant of claim 16, wherein the channel is open along a length that extends to a distal end of the body.

24. An implant designed to relieve excessive intraocular pressure, the implant comprising:
a biocompatible metal stent shaped to be partially circumferentially positioned within a length of Schlemm's canal in a living human eye;
wherein the stent comprises a non-tubular open shape to provide stenting support for the patency of Schlemm's canal and to improve flow of aqueous humor into Schlemm's canal after implantation of the stent;
wherein at least one cross-section of the stent approximates a partial circumference of a circle having an inner diameter between about 100 micrometers and 500 micrometers.

25. The implant of claim 24, wherein a portion of the stent is oriented to be positioned in an anterior chamber of the eye after implantation.

26. The implant of claim 24, wherein the stent has a non-linear shape before insertion into the eye.

27. The implant of claim 24, wherein the stent is elongate and further includes multiple holes along its length.

28. The implant of claim 27, wherein at least some of the holes are oval-shaped.

29. The implant of claim 24, wherein the non-tubular open shape of the stent is disposed to facilitate flow of aqueous humor into one or more collecting channels in the eye.

30. The implant of claim 24, wherein the at least one cross-section is approximately semi-circular.

31. The implant of claim 24, wherein the stent is oriented so as to open toward one or more of the collecting channels when located within Schlemm's canal.

32. A surgical method for relieving excessive intraocular pressure by implanting a medical device in an eye, the method comprising:
inserting a non-luminal open stent into a living human eye, wherein at least one cross-section of the stent approximates a partial circumference of a circle having an inner diameter between about 100 micrometers and 500 micrometers;
creating an incision in a trabecular meshwork of the eye;
positioning the stent through the incision so that the stent is partially located in an anterior chamber of the eye and partially located within a circumferential length of Schlemm's canal in the eye;
leaving the stent in the eye as a permanent implant to permit increased flow of aqueous humor from the anterior chamber into Schlemm's canal.

33. The method of claim 32, wherein the stent provides stenting support for the patency of Schlemm's canal.

34. The method of claim 32, wherein the stent is oriented to open toward one or more collecting channels of the eye to facilitate flow of aqueous humor.

35. The method of claim 34, wherein the portion of the stent positioned in Schlemm's canal further includes multiple openings along its length through which aqueous humor is permitted to flow from the anterior chamber into Schlemm's canal.

36. The method of claim 32, wherein the stent is flexible and comprises a biocompatible metal.

37. The method of claim 32, wherein the stent has a non-linear shape before insertion into the eye.

38. An implant for relieving excessive intraocular pressure, the implant comprising:
a non-luminal, elongated body of biocompatible material for implantation in a living human eye, the body comprising,
a channel shaped to be at least partially positioned within a circumferential length of Schlemm's canal, wherein the channel is at least partially open along a length of the body and is oriented to open toward one or more collecting channels when implanted in the eye; and
a portal that is generally adjacent to an inner wall of Schlemm's canal when the body is implanted in the eye, so as to allow flow of aqueous humor from an anterior chamber through trabecular meshwork and into Schlemm's canal.

39. The implant of claim 38, wherein the portal in the body is oval-shaped.

40. The implant of claim 39, wherein the body includes multiple oval-shaped portals along the length of the channel.

41. The implant of claim 38, wherein at least one cross-section of the body approximates a partial circumference of a circle having an inner diameter between about 100 micrometers and 500 micrometers.

42. The implant of claim 38, wherein the channel is open along a length that extends to a distal end of the body.

\* \* \* \* \*